United States Patent
Bhagavatula et al.

(10) Patent No.: US 8,857,220 B2
(45) Date of Patent: Oct. 14, 2014

(54) METHODS OF MAKING A STUB LENS ELEMENT AND ASSEMBLIES USING SAME FOR OPTICAL COHERENCE TOMOGRAPHY APPLICATIONS

(75) Inventors: Venkata Adiseshaiah Bhagavatula, Big Flats, NY (US); John Himmelreich, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 308 days.

(21) Appl. No.: 13/403,446

(22) Filed: Feb. 23, 2012

(65) Prior Publication Data
US 2013/0219969 A1 Aug. 29, 2013

(51) Int. Cl.
B29D 11/00 (2006.01)

(52) U.S. Cl.
USPC .......... 65/387; 65/378; 65/63; 65/64; 65/296; 264/2.7

(58) Field of Classification Search
CPC .............. A61B 5/0084; A61B 5/0066; B02D 911/00692
USPC .................. 65/378, 387, 63, 64, 296; 264/2.7
See application file for complete search history.

(56) References Cited

U.S. PATENT DOCUMENTS

| | | | |
|---|---|---|---|
| 5,321,501 A | 6/1994 | Swanson et al. | |
| 6,134,003 A | 10/2000 | Tearney et al. | |
| 6,445,939 B1 | 9/2002 | Swanson et al. | |
| 6,564,087 B1 | 5/2003 | Pitris et al. | |
| 6,891,984 B2 | 5/2005 | Petersen et al. | |
| 6,904,197 B2 | 6/2005 | Bhagavatula et al. | |
| 7,228,033 B2 | 6/2007 | Bhagavatula et al. | |
| 7,241,286 B2 | 7/2007 | Atlas | |
| 7,258,495 B1 | 8/2007 | Hughes, Jr. et al. | |
| 7,944,556 B2 | 5/2011 | Smous et al. | |
| 7,952,718 B2 | 5/2011 | Li et al. | |
| 8,169,618 B2 | 5/2012 | Inoue | |
| 8,186,109 B2 | 5/2012 | Warminsky | |
| 2002/0009261 A1* | 1/2002 | Bhagavatula et al. | 385/35 |
| 2004/0017961 A1 | 1/2004 | Petersen et al. | |

(Continued)

FOREIGN PATENT DOCUMENTS

| | | |
|---|---|---|
| EP | 0575993 | 12/1993 |
| EP | 2133781 | 12/2009 |
| WO | WO 2011/069630 | 6/2011 |

OTHER PUBLICATIONS

Xi, Huo, et al., "High Resolution OCT balloon imaging catheter with astigmatism correction", Optic Letters, vol. 34, No. 13, p. 1943-1945 (Jul. 1, 2009).

(Continued)

*Primary Examiner* — Queenie Dehghan
(74) *Attorney, Agent, or Firm* — Svetlana Short

(57) ABSTRACT

Methods of making a stub lens element and assemblies for coherence tomography (OCT) applications are disclosed. The method of making the stub lens element includes drawing a rod of optical material and processing the drawn rod to form a lens integrally connected to a stub section. The methods also include operably supporting an optical fiber and a stub lens element in a cooperative optical relationship to form a stub lens sub-assembly. The methods also include operably supporting the stub lens sub-assembly and a light-deflecting member in a cooperative optical relationship to form a probe optical assembly that has a folded optical path.

20 Claims, 20 Drawing Sheets

(56) References Cited

U.S. PATENT DOCUMENTS

| | | | |
|---|---|---|---|
| 2004/0240786 A1* | 12/2004 | Gafsi et al. | 385/33 |
| 2005/0122601 A1* | 6/2005 | Takeuchi et al. | 359/831 |
| 2005/0123240 A1* | 6/2005 | Seto et al. | 385/35 |
| 2005/0201662 A1 | 9/2005 | Petersen et al. | |
| 2006/0067620 A1 | 3/2006 | Shishkov et al. | |
| 2007/0165981 A1* | 7/2007 | Tanaka et al. | 385/33 |
| 2009/0190833 A1 | 7/2009 | Alvino et al. | |
| 2009/0190883 A1 | 7/2009 | Kato et al. | |
| 2009/0198125 A1 | 8/2009 | Nakabayashi et al. | |
| 2009/0262361 A1* | 10/2009 | Tanioka et al. | 356/479 |
| 2010/0253949 A1 | 10/2010 | Adler et al. | |
| 2011/0122410 A1 | 5/2011 | Wang et al. | |
| 2012/0099112 A1* | 4/2012 | Alphonse et al. | 356/479 |

OTHER PUBLICATIONS

Cabibihan, J-J et al., "Prosthetic finger phalanges with lifelike skin compliance for low-force social touching interactions", Journal of NeuroEngineering and Rehabilitation 2011, 8:16.

Cabibihan, J-J et al., "Towards Humanlike Social Touch for Sociable Robitics and Prosthetics: Comparisons on the Compliance, Conformance and Hysteresis of Synthetic and Human Fingertip Skins", International Journal of Social Robotics, vol. 1, Issue 1, pp. 29-40 (2009).

* cited by examiner

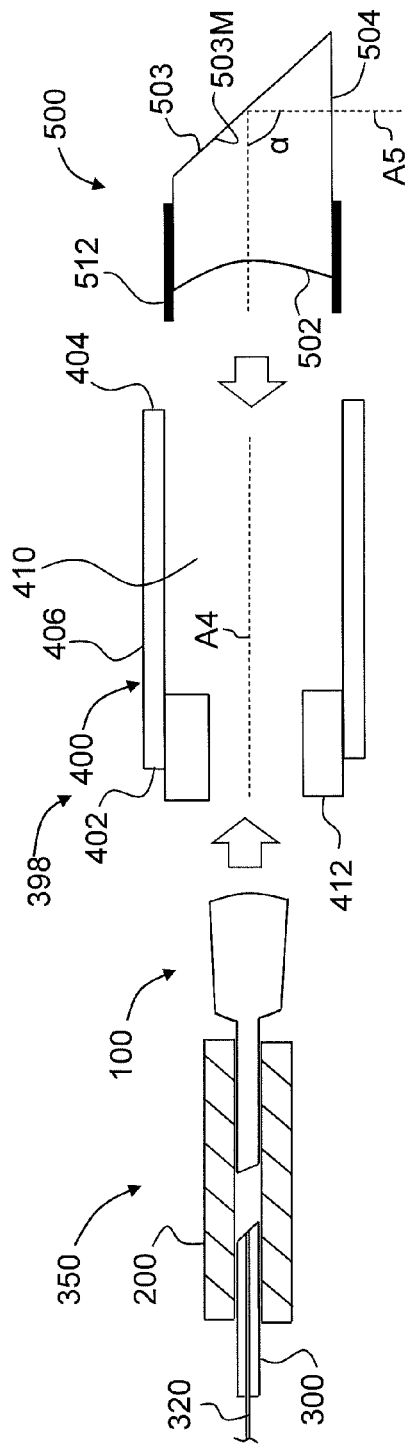
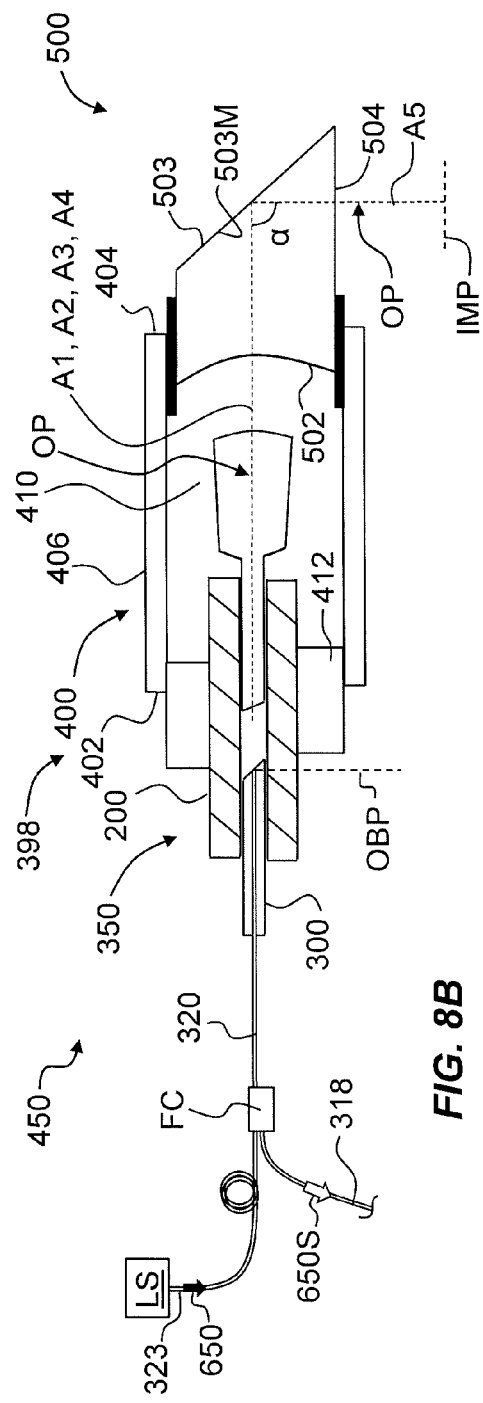
FIG. 8A
FIG. 8B

METHODS OF MAKING A STUB LENS ELEMENT AND ASSEMBLIES USING SAME FOR OPTICAL COHERENCE TOMOGRAPHY APPLICATIONS

CROSS-REFERENCE TO RELATED APPLICATIONS

This application is related to U.S. patent application Ser. No. 13/403,465, entitled "Stub lens assemblies for use in optical coherence tomography systems," and to U.S. patent application Ser. No. 13/403,485, entitled "Probe optical assemblies and probes for optical coherence tomography," both of which have been filed on the same day as the present application and both of which are incorporated by reference herein.

FIELD

The present invention relates to optical coherence tomography, and in particular to methods of making a stub lens element and assemblies using same for optical coherence tomography applications.

BACKGROUND ART

Optical coherence tomography (OCT) is used to capture a high-resolution cross-sectional image of scattering biological tissues and is based on fiber-optic interferometry. The core of an OCT system is a Michelson interferometer, wherein a first optical fiber is used as a reference arm and a second optical fiber is used as a sample arm. The sample arm includes the sample to be analyzed as well as a probe that includes optical components. An upstream light source provides the imaging light. A photodetector is arranged in the optical path downstream of the sample and reference arms.

Optical interference of light from the sample arm and the reference arm is detected by the photodetector only when the optical path difference between the two arms is within the coherence length of the light from the light source. Depth information from the sample is acquired by axially varying the optical path length of the reference arm and detecting the interference between light from the reference arm and scattered light from the sample arm that originates from within the sample. A three-dimensional image is obtained by transversely scanning in two dimensions the optical path in the sample arm. The axial resolution of the process is determined by the coherence length.

To obtain a suitably high-resolution 3D image, the probe typically needs to meet a number of specific requirements, which can include: single-mode operation at a wavelength that can penetrate to a required depth in the sample; a sufficiently small image spot size; a working distance that allows the light beam from the probe to be focused on and within the sample; a depth of focus sufficient to obtain good images from within the sample; a high signal-to-noise ratio (SNR); and a folded optical path that directs the light in the sample arm to the sample.

In addition, the probe needs to fit within a catheter, which is then snaked through blood vessels, intestinal tracks, esophageal tubes, and like body cavities and channels. Thus, the probe needs to be as small as possible while still providing robust optical performance. Furthermore, the probe operating parameters (spot size, working distance, etc.) will substantially differ depending on the type of sample to be measured and the type of measurement to be made.

SUMMARY

An aspect of the disclosure includes a method of making a stub lens element. The method includes heating an end of a rod of optical material that has a central axis and a width dimension D1 in a range between 250 microns and 1000 microns to form a bulbous rod end having a width dimension D2 in a range between 300 microns and 2500 microns wherein the remaining rod defines a stem section. The method also includes removing a portion of the optical material from the bulbous rod end to reduce the width dimension D2 to form a lens having an on-axis lens surface. The method further includes cutting the stem section to define an angled proximal end opposite the on-axis lens surface.

In one example, the method includes forming the stub lens element so that it has an axial length L from the angled proximate end to the lens surface that is in the range $0.5 \text{ mm} \leq L \leq 5 \text{ mm}$. In another example, the method includes forming the lens surface to be spherical and having a radius of curvature R2 in the range $0.15 \text{ mm} \leq R2 \leq 1.5 \text{ mm}$.

Another aspect of the disclosure includes the method as described above and further includes engaging the stub lens element with a first sleeve having first and second ends, an outer surface, a central axis and a central channel that runs along the central axis and that is open at the first and second ends, with the stub section fixed within the central channel. An example first sleeve comprises a first section of capillary tubing. The first sleeve can include a slot in the outer surface that leads to the central channel, and the method can include fixing the stub section within the central channel of the first sleeve by introducing an adhesive material into the slot.

Another aspect of the disclosure includes the method as described above and further includes inserting an optical fiber ferrule that operably supports an optical fiber into the first end of the first sleeve so that an end of the optical fiber resides adjacent the angled proximal end of the stub section within the central channel.

Another aspect of the disclosure includes the method as described above and further includes aligning the optical fiber and the stub lens element. This includes focusing light emitted by the optical fiber end at a working distance from the lens surface, and forming an image spot having an image mode field diameter. The method also includes adjusting at least one of the optical fiber end and the stub lens element to minimize the size of the image mode field diameter. This method can additionally include detecting the image spot with a photodetector to form an electrical signal, and processing the electrical signal to determine when the image mode field diameter $MFD_{IM}$ is at a minimum.

Another aspect of the disclosure the method as described above and further includes supporting the optical fiber ferrule, the first sleeve and the stub lens element at a first end of a second sleeve that includes a second end, a central axis and interior open at the first and second ends. The method also includes disposing a light-deflecting member at the second end of the second sleeve and adjacent the lens surface of the stub optical element so as to be in a cooperative optical relationship therewith, thereby forming a probe optical assembly. The second sleeve can be, for example, a section of capillary tubing.

The method can also include enclosing the probe optical assembly in a transparent jacket having a diameter D3 in the range $1 \text{ mm} \leq D3 \leq 2 \text{ mm}$. In the case where the transparent jacket has a curved outer surface that has a first optical power, the method can further include configuring the light-deflecting member to have a second optical power that compensates for the first optical power.

It is to be understood that both the foregoing general description and the following Detailed Description represent embodiments of the disclosure, and are intended to provide an overview or framework for understanding the nature and character of the disclosure as it is claimed. The accompanying drawings are included to provide a further understanding of the disclosure, and are incorporated into and constitute a part of this specification. The drawings illustrate various embodiments of the disclosure and together with the description serve to explain the principles and operations of the disclosure.

Additional features and advantages of the disclosure are set forth in the detailed description that follows, and in part will be readily apparent to those skilled in the art from that description or recognized by practicing the disclosure as described herein, including the detailed description that follows, the claims, and the appended drawings.

The claims are incorporated into and constitute part of the Detailed Description set forth below.

Any numerical provided herein are inclusive of the limits provided unless otherwise stated.

BRIEF DESCRIPTION OF THE DRAWINGS

FIG. 8A is a cross-sectional view that shows the stub lens assembly and a light-deflecting member along with a support member in the form of an outer sleeve, in the process of fabricating a probe optical assembly to be used to form an OCT probe;

FIG. 8B shows the stub lens assembly, light-deflecting member and outer sleeve operably arranged to form the probe optical assembly;

Figure 1:
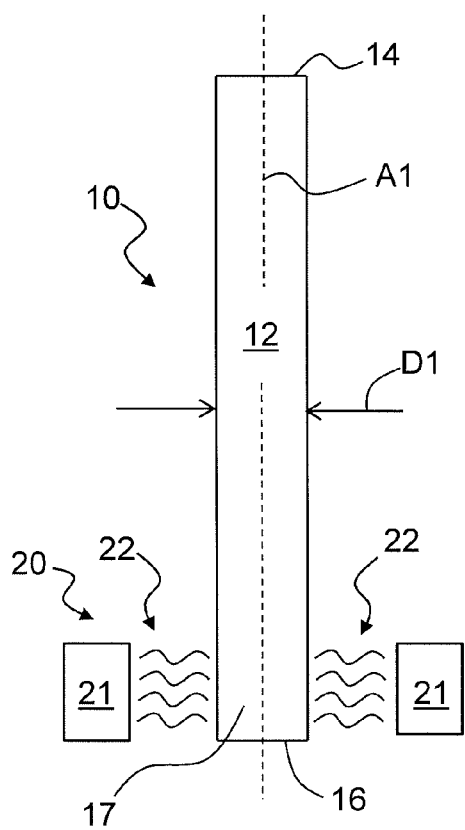
FIG. 1 is a side view of a rod made of an optical material, shown with one of its ends operably arranged relative to a heat source.

Additional features and advantages of the disclosure are set forth in the Detailed Description that follows and will be apparent to those skilled in the art from the description or recognized by practicing the disclosure as described herein, together with the claims and appended drawings. It will be understood that the illustrations are for the purpose of describing particular embodiments and are not intended to limit the disclosure or appended claims thereto. The drawings are not necessarily to scale, and certain features and certain views of the drawings may be shown exaggerated in scale or in schematic in the interest of clarity and conciseness.

Cartesian coordinates are shown in certain of the Figures for the sake of reference and are not intended as limiting with respect to direction or orientation.

DETAILED DESCRIPTION

In the following description, like reference characters designate like or corresponding parts throughout the several views shown in the figures. Unless otherwise specified, a range of values, when recited, includes both the upper and lower limits of the range. As used herein, the indefinite articles "a," "an," and the corresponding definite article "the" mean "at least one" or "one or more," unless otherwise specified.

The mode field diameter MFD is a measure of the spot size or beam width of light propagating in a single mode fiber. The mode field diameter MFD is a function of the source wavelength, fiber core radius r and fiber refractive index profile. In an example, the mode field diameter MFD can be measured as the full width at 13.5% of the peak power for a best fit Gaussian beam, while in another example it can be measured by using the Peterman II method, where MFD=2w, and $$w^2 = 2 \frac{\int_0^\infty E^2 r\, dr}{\int_0^\infty (dE/dr)^2 r\, dr}$$

wherein E is the electric field distribution in the optical fiber and r is the radius of the optical fiber core.

With reference to the Figures discussed in greater detail below, the mode field diameter MFD is also referred to herein as a property of an image spot 652 formed at a working distance WD by a probe optical assembly 450 and in this instance is referred to as the image mode field diameter $MFD_{IM}$, or "image $MFD_{IM}$" for short, since the probe optical assembly images an end 324 of an optical fiber 320, as explained below. The mode field diameter MFD associated with optical fiber 320 is thus called the fiber mode field diameter $MFD_F$, or "fiber $MFD_F$" for short. An example range for the working distance WD (see FIG. 9A) is 5 mm WD 15 mm. An example image $MFD_{IM}$ is in the range of 15 microns $MFD_{IM}$≤100 microns.

Stub Lens Element

FIG. 1 is a side view of a rod 10 made of an optical material. Example optical materials for rod 10 include PYREX® glass, silica, VYCOR® glass or an optical glass. An example rod 10 has a cylindrical shape with any one of a number of possible cross-sectional shapes, such as circular, elliptical, polygonal, etc. The rod 10 has a body 12 that defines a central axis A1, a proximal end 14, a distal end 16, and a cross-sectional dimension (e.g., a diameter) D1. An example diameter D1 for rod 10 is in the range of 250 microns and 1000 microns for a circular cross-sectional shape.

Figure 2:
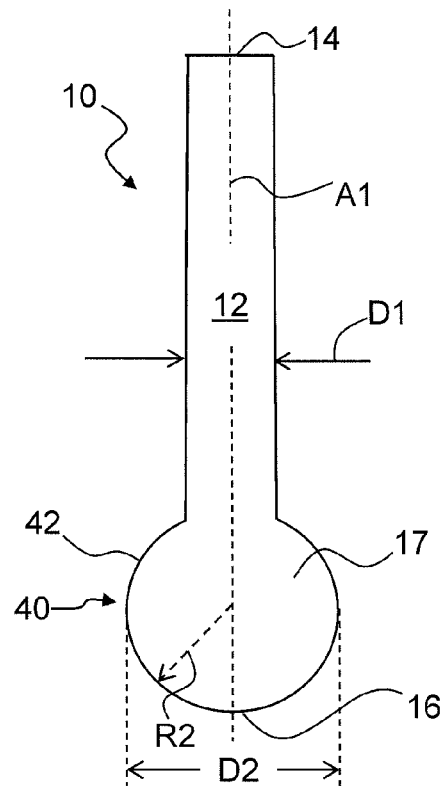
FIG. 2 is similar to FIG. 1 and shows a stub lens element formed by heating one end of the rod to form a bulbous end portion that defines a lens having a lens surface.

FIG. 1 also shows rod distal end 16 operably disposed relative to a heat source 20. An example heat source 20 includes at least one heating member 21 that generates heat 22. An example heating member 21 includes an electrical arc, a laser, a joule-heating element, a flame, a ring burner, etc. The heat 22 is applied to a distal end portion 17 of rod 10 adjacent distal end 16 while the rod is disposed vertically, i.e., with axis A1 oriented in the direction of gravity. The heat 22 is sufficient to make the distal end portion 17 flow, whereupon surface tension causes the distal end portion to become bulbous, as illustrated in FIG. 2. Depending on the cross section of rod 10 and processing conditions, the shape can be spherical, ellipsoid, etc. The now bulbous distal end portion 17 has a diameter D2, which in an example is in the range of about 300 microns to 2,500 microns. In an example, a rod 10 made of silica glass and having a diameter D1 of about 500 microns and having a circular cross-sectional shape allows for diameter D2 to be about 1.5 mm.

The bulbous distal end portion 17 defines a lens 40 having a lens surface 42. The size of lens 40 and the shape of lens surface 42 can be controlled by controlling the rod-end melting process, e.g., by controlling at least one of: the amount of heat 22 provided by heat source 20, the feed rate of rod 10 into heat 22, the rotation of the rod about its central axis A1, and the distance over which the rod is lowered into the heat. In particular, lens surface 42 can be made spherical to a high degree of accuracy using this process, though aspherical lens surface shapes can be made as well. In an example, where lens surface 42 is spherical, it can have a radius of curvature R2 in the range 0.15 mm≤R2≤1.5 mm (see FIG. 3A and FIG. 4A).

Figure 3A:
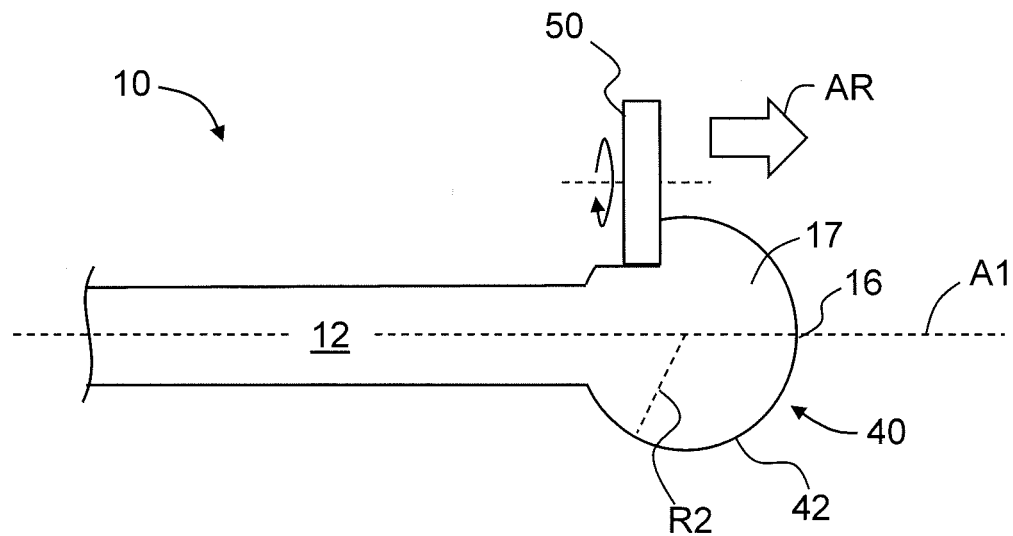
FIG. 3A is similar to FIG. 2 and shows the stub lens element in the process of having its lens reduced in size in the lateral dimension by mechanical means.
Figure 3B:
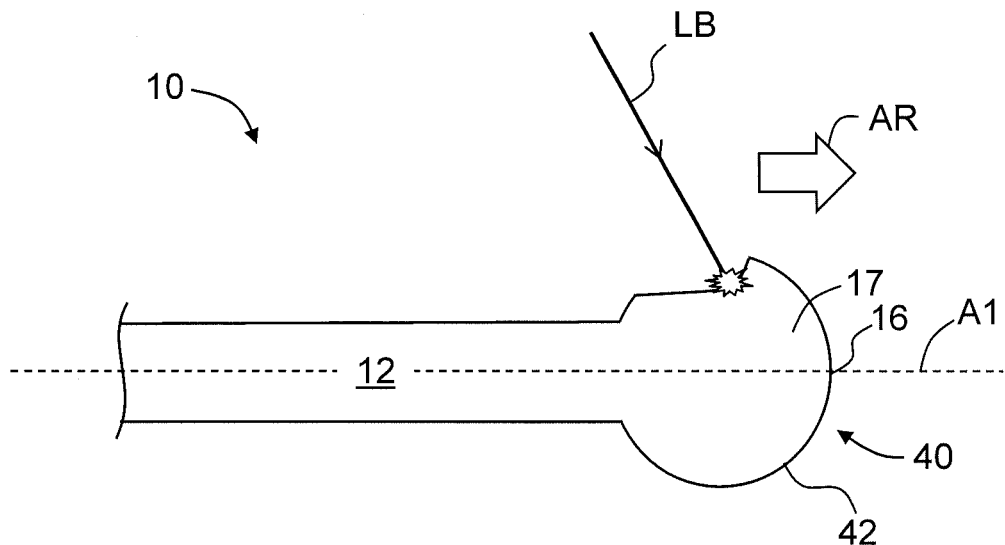
FIG. 3B is similar to FIG. 3A and shows the stub lens element having its lens reduced in size in the lateral dimension via laser processing with a laser beam.

In an example, further processing is carried out to change the shape of lens 40, and in particular to reduce the lateral dimension of the lens. FIG. 3A is similar to FIG. 2, and illustrates an example embodiment wherein lens 40 is in the process of being reduced in size in the lateral dimension via mechanical grinding by a mechanical grinder 50. FIG. 3B is similar to FIG. 3A and illustrates another example of lens 40 being reduced in size in the lateral dimension via laser processing by a laser beam LB. Arrows AR in FIG. 3A and FIG. 3B show the direction of motion of mechanical grinder 50 and laser beam LB, respectively.

Figure 4A:
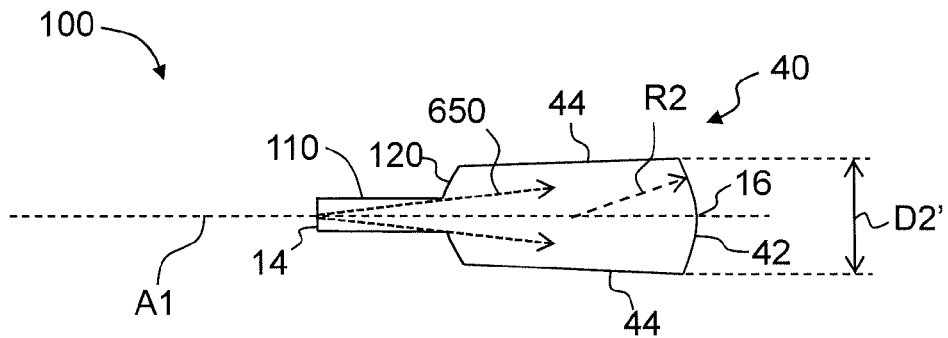
FIG. 4A and FIG. 4B illustrate examples of the stub lens element formed by processing the lens to reduce its lateral dimension.
Figure 4B:
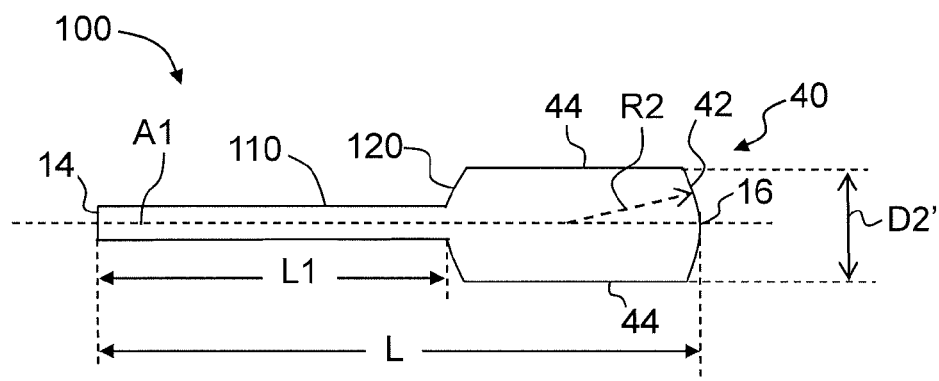

FIG. 4A and FIG. 4B illustrate examples of a resultant stub lens element 100 formed by processing lens 40 such that its lateral dimension is reduced. In one example, processed lens 40 has a reduced lateral dimension D2' in the range about 600 microns to 1 mm, while in another example the reduced lateral dimension D2' is in the range 700 microns to 800 microns. With reference to FIG. 4B, in an example, stub lens element 100 has an axial length L from proximate end 14 to lens surface 42 that is in the range 0.5 mm≤L≤5 mm.

The stub lens element 100 includes stub section 110 formed by the unaffected portion of rod 10 and the reduced-size lens 40, which hereinafter is referred to as stub lens 40. The stub lens 40 has a non-lens outer surface portion 44 adjacent lens surface 42. The stub section 110 serves as a handle for handling stub lens element 100 and can be cut to have a length suited for its particular application. The stub lens element 100 of FIG. 4A has a stub lens 40 with a conic or flared outer surface portion 44, while the stub lens of FIG. 4B has a cylindrical outer surface portion. As shown in FIG. 4B, stub section 110 has a length L1=L−2·(R2).

As illustrated in the example stub lens element 100 of FIG. 4A, the flared shape of lens 40 is employed to accommodate light 650 that diverges as it passes from proximal end 14 to distal end 16. The stub lens 40 of FIG. 4A also shows a relatively short stub section 110 that can be formed by the aforementioned cutting after stub lens element 100 is formed as described above. A transition portion 120 forms the connection between stub section 110 and stub lens 40.

Figure 4C:
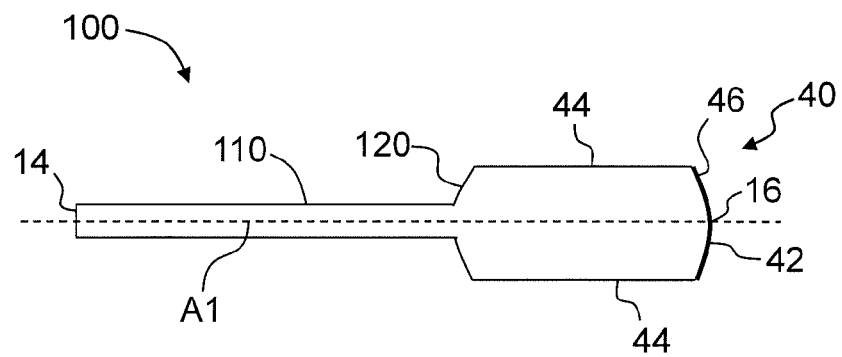
FIG. 4C is similar to FIG. 4B and shows an example where the lens surface includes an anti-reflection coating.

In examples, lens surface 42 of stub lens 40 can be spherical or aspherical. Example aspherical surfaces include biconic, parabolic, hyperbolic, etc. The shape of lens surface 42 can be defined by controlling the above-described melt process. In an example, an anti-reflection coating 46 can be applied to lens surface 42, as illustrated in FIG. 4C.

Figure 5A:
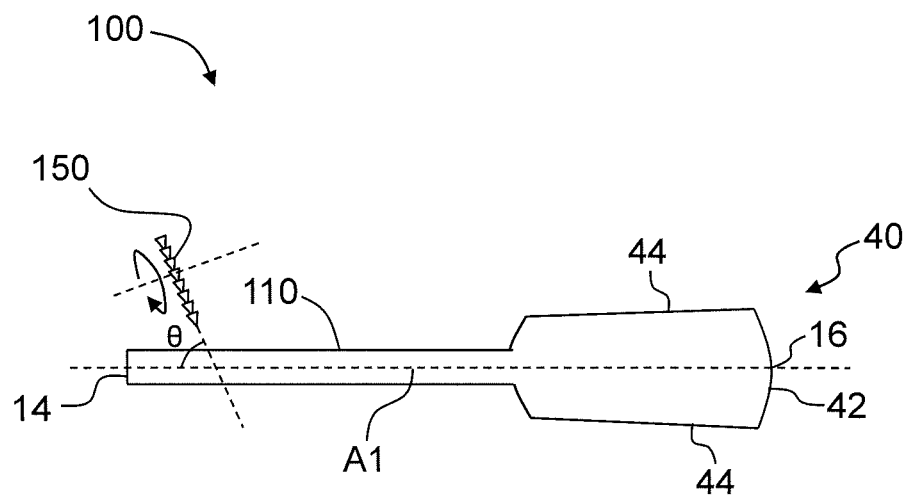
FIG. 5A and FIG. 5B are similar to FIG. 4A, with FIG. 5A showing a cutting tool being used to cut the stub section to form an angled proximal end, the resulting angled proximal end being shown in FIG. 5B.
Figure 5B:
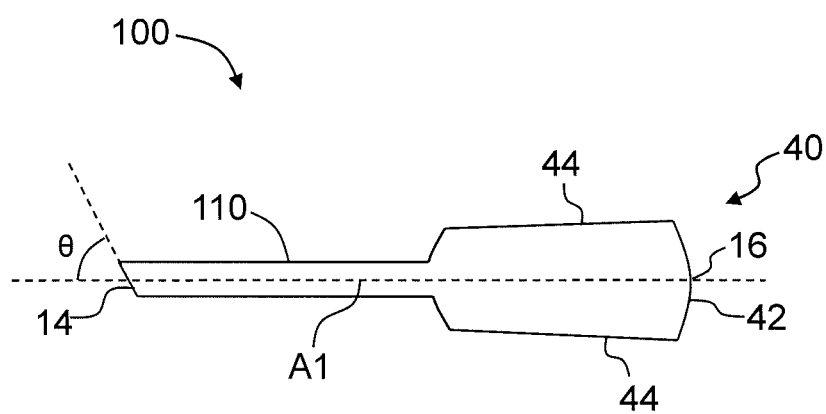

FIG. 5A is similar to FIG. 4A and shows a cutting tool 150 being used to cut stub section 110 of stub lens element 100 to form an angled proximal end 14 that defines an angle θ relative to axis A1, as shown in FIG. 5B. The angled proximal end 14 can serve to reduce back reflections when stub lens element 100 is used in an OCT probe, as described in greater detail below. An example angle θ is in the range from about 5° to about 12°.

OCT Probe Assemblies

Figure 6A:
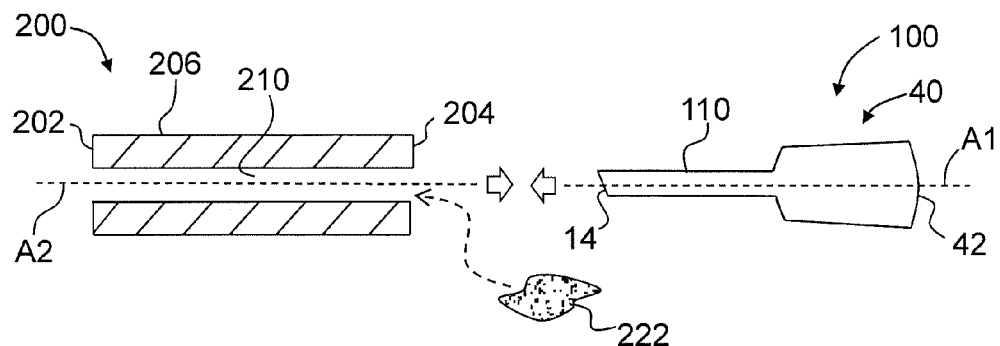
FIG. 6A is a cross-sectional view of an example stub lens element shown along with a cylindrical sleeve.

Aspects of the disclosure are directed to OCT probes and assemblies used in such probes. FIG. 6A is a cross-sectional view of an example stub lens element 100 along with a cylindrical sleeve 200. The cylindrical sleeve 200 has a central axis A2, first and second ends 202 and 204, an outer surface 206, and a central channel 210 that runs along the central axis and that is open at the first and second ends. The central channel 210 is sized to accommodate stub section 110 of stub lens element 100. The sleeve 200 can be made of any rigid material, with glass, plastic and metal being some exemplary materials. An exemplary sleeve 200 comprises a section of precision capillary tubing, which can be drawn down to a select size from a much larger tube using a process similar to a redraw process used to make optical fibers. As sleeve 200 is later incorporated into another larger sleeve as is explained below, it is referred to hereinafter as inner sleeve 200.

Figure 6B:
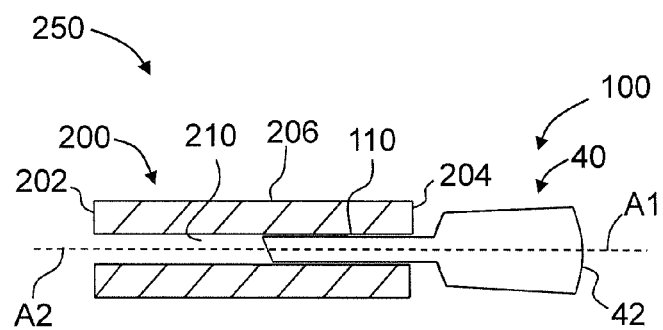
FIG. 6B is similar to FIG. 6A and shows the stub element operably engaged with the sleeve to form a stub lens subassembly.

FIG. 6B is similar to FIG. 6A and shows stub lens element 100 engaged with inner sleeve 200 by inserting stub section 110 into inner sleeve central channel 210 at sleeve second end 204, thereby forming a stub lens sub-assembly 250. In an example, an adhesive material 222 can be used to secure stub section 110 in central channel 210. When stub lens element 100 is engaged with inner sleeve 200, the stub lens element axis A1 is substantially co-axial with inner sleeve axis A2. The stub lens sub-assembly 250 is thus configured to operably support optical fiber end 324 and stub lens element 100 in a cooperative optical relationship.

Figure 6C:
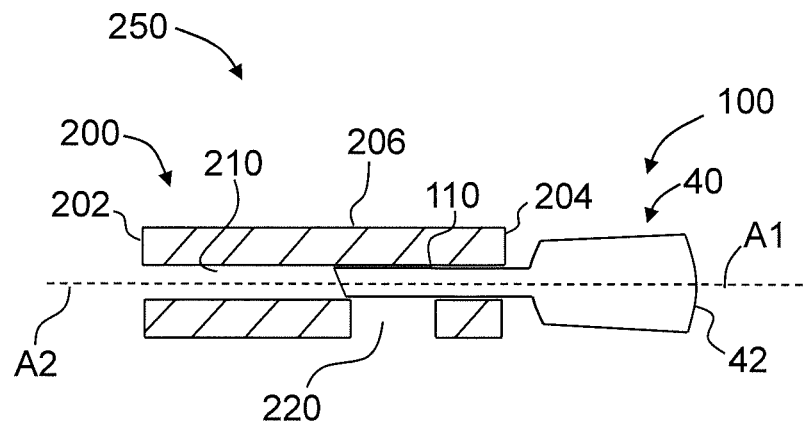
FIG. 6C is similar to FIG. 6B and shows an example sleeve that includes a slot that leads from the sleeve outer surface to the sleeve central channel.
Figure 6D:
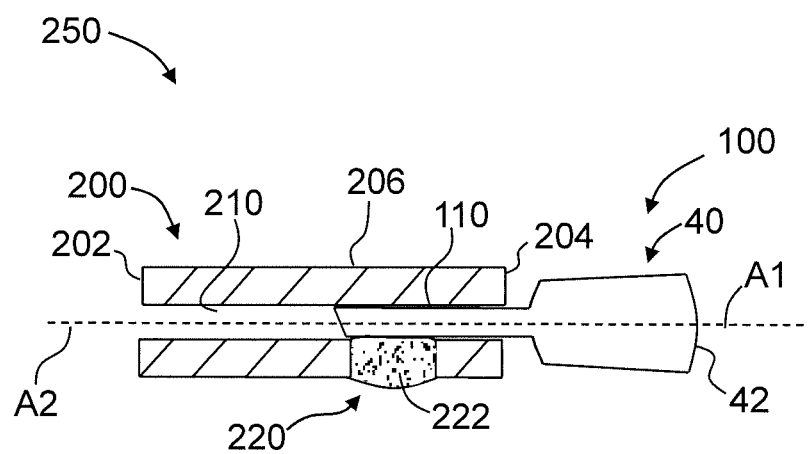
FIG. 6D is similar to FIG. 6C and shows an adhesive material disposed in the slot and that serves to secure the stub section of the stub lens element to the sleeve.

FIG. 6C is similar to FIG. 6B and shows an example wherein inner sleeve 200 includes a slot 220 formed in inner sleeve outer surface 206 that leads to central channel 210. FIG. 6D is similar to FIG. 6C and shows adhesive material 222 disposed in slot 220. Adhesive material 222 is introduced into slot 220 and contacts stub section 110 of stub lens element 100. This serves to secure (fix) the stub section to inner sleeve 200, and providing an alternative to adding the adhesive material to central channel 210 from one of its ends. Once adhesive material 222 hardens, it can be ground, polished or otherwise processed to make its outer surface conform to outer surface 206 of inner sleeve 200. The slot 220 may be formed in inner sleeve 200 by laser beam LB or by mechanical means, e.g., cutting or grinding.

As discussed below, it may be desirable to introduce adhesive material 222 between stub lens element 100 and an optical fiber ferrule, introduced and discussed below. If channel 210 of inner sleeve 200 does not have a means for air to escape, then inserting adhesive material 222 into the channel can be problematic. So slot 220 can serve the additional function of providing a means for air to escape from channel 210 during the fabrication process.

Figure 7A:
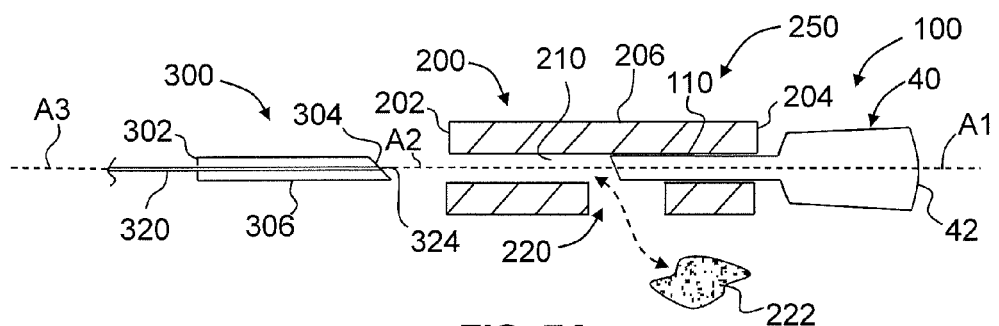
FIG. 7A is similar to FIG. 6B and shows the stub lens sub-assembly of FIG. 6A along with an example optical fiber ferrule.
Figure 7B:
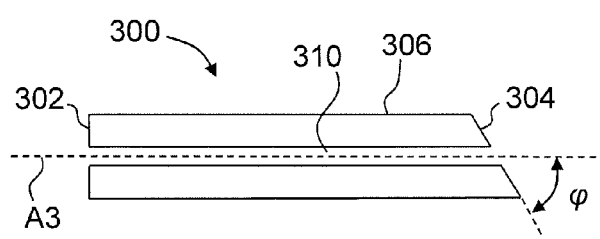
FIG. 7B is a close-up view of the optical fiber ferrule of FIG. 7A.

FIG. 7A is similar to FIG. 6B and shows stub lens subassembly 250 along with an optical fiber ferrule ("ferrule") 300, and FIG. 7B is a close-up view of ferrule 300. The ferrule 300 has a central axis A3, first and second ends 302 and 304, an outer surface 306, and a central bore 310 that runs along the central axis and that is open at the first and second ends. The central bore 310 is sized to fit into channel 210 of inner sleeve 200. The ferrule 300 can be made of any rigid material, with glass, plastic and metal being some exemplary materials. In an example, ferrule 300 comprises a section of precision capillary tubing. An example diameter of central bore 310 is about 128 microns, and an example outer diameter of ferrule 300 is about 500 microns.

In an example, ferrule end 304 is angled at an angle φ relative to central axis A3. The central bore 310 of ferrule 300 is sized to accommodate an optical fiber 320, which in an example is a single-mode optical fiber. The 3ptical fiber 320 includes end 324, which resides substantially at angled ferrule end 304. In the example where ferrule end 304 is angled, optical fiber end 324 can also be angled at the same angle φ as the ferrule end. This can be accomplished by inserting optical fiber 320 into ferrule 300 when it has a non-angled end 304, and then forming the angled ferrule end 304 by a cutting and polishing process that serves also to cut and polish optical fiber end 324.

Figure 7C:
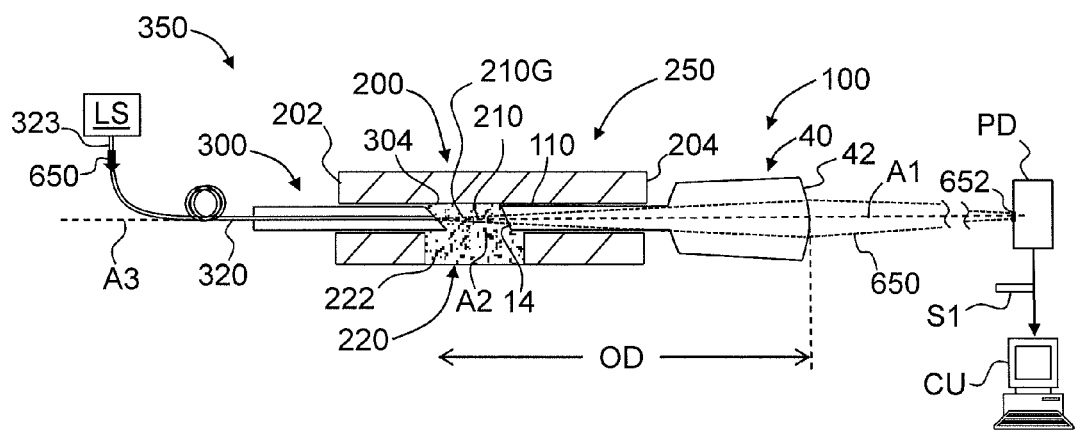
FIG. 7C shows the optical fiber ferrule with an optical fiber secured therein, engaged with the central channel of the sleeve to form a stub lens assembly, and also shows a photodetector used to measure the mode field diameter of the focused light when performing alignment of the stub lens element relative to the optical fiber.

FIG. 7C shows ferrule 300, with optical fiber 320 secured therein, engaged with central channel 210 of inner sleeve 200 at inner sleeve end 202, so that axes A1, A2 and A3 are all substantially co-axial. The angled ferrule end 304 and angled end 14 of stub section 110 define a gap 210G within central channel 210 between the respective angled ends. In an example, gap 210G can be filled with the aforementioned adhesive material 222 (not shown), e.g., in the form of an index-matching epoxy, to further reduce the back reflections and reduce the sensitivity of the rotational alignment of opposing angled ends. The combination of stub lens subassembly 250, ferrule 300 and optical fiber 320 form a stub lens assembly 350. The stub lens assembly 350 has an object distance OD, which is defined as the axial distance between optical fiber end 324 and lens surface 42 of lens 40. In an example, object distance OD is in the range 0.5 mm≤OD≤5 mm, and in a more specific example is 1 mm≤OD≤3 mm.

With continuing reference to FIG. 7C, in an example, during the fabrication of stub lens assembly 350, one of the fabrication steps includes measuring the image $MFD_{IM}$. This can be accomplished using, for example, a photodetector PD in the form of a beam-scanning apparatus or a digital camera. A light source LS is optically connected to an end 323 of optical fiber 320. The photodetector PD is used to measure the size of image spot 652 as formed by light 650 emanating from optical fiber end 324 and being focused by stub lens element 100 at the anticipated working distance WD. The axial position of at least one of ferrule 300 and stub lens element 100 can be adjusted until the object distance OD that minimizes the image $MDF_{IM}$ is determined.

In an example, photodetector PD generates an electrical signal S1 that is representative of the detected image $MFD_{IM}$, and this electrical signal is analyzed (e.g., via a computer CU operably connected to photodetector PD) to assess the optimum object distance OD. Once the optimum object distance OD is established, then ferrule 300 and stub lens element 100 are fixed in place within inner sleeve 200 using, e.g., adhesive material 222, which can be a UV-curable epoxy. In one example, stub lens element 100 is fixed relative to inner sleeve 200 prior to the image $MFD_{IM}$ measurement, and only the axial position of ferrule 300 is adjusted. In an example fabrication step, gap 210G can be filled with the aforementioned index-matching material, e.g., UV-curable adhesive material 222, through slot 220 (see FIGS. 7A and 7C).

In an example embodiment, stub lens assembly 350 is operably supported by a support member. FIG. 8A is a cross-sectional view that shows stub lens assembly 350 and a light-deflecting member 500 having an axis A5 and arranged relative to a support member 398 in the form of an outer sleeve 400 in the process of forming a probe optical assembly 450, as shown in FIG. 8B. The support member 398 is configured to operably support stub lens sub-assembly 350 and light-deflecting member 500 in a cooperative optical relationship that defines folded optical path OP.

The light-deflecting member 500 is shown and discussed herein below as a prism by way of illustration. In an alternate example, light-deflecting member 500 comprises a mirror. The outer sleeve 400 has a central axis A4, first and second ends 402 and 404, an outer surface 406, and an interior 410 that runs along the central axis and that is open at the first and second ends. The interior 410 is configured to accommodate at end 402 stub lens assembly 350 and at end 404 light-deflecting member 500. In an example, outer sleeve 400 includes a retaining feature 412 disposed within interior 410 at end 402, with the retaining feature configured to retain inner sleeve 200 of stub lens assembly 350. The outer sleeve 400 can be made of any rigid material, with glass, plastic and metal being exemplary materials. In an example, outer sleeve 400 comprises a section of precision capillary tube.

With continuing reference to FIG. 8A, light-deflecting member 500 includes a cylindrically curved front surface 502, a planar angled surface 503 that defines a total-internal-reflection (TIR) mirror 503M, and a planar bottom surface 504. The light-deflecting member central axis A5 is folded by TIR mirror 503M. The angle of deflection a can be in the range between 90 and 100 degrees.

The light-deflecting member 500 is shown along with a retaining feature 512 that serves to retain the light-deflecting member in interior 410 at end 404 of outer sleeve 400 when the light-deflecting member and the outer sleeve are operably engaged. In an example, retaining feature 512 is simply adhesive material 222.

FIG. 8B shows stub lens assembly 350 and light-deflecting member 500 operably engaged with outer sleeve 400 at respective ends 402 and 404, thereby forming the aforementioned probe optical assembly 450. The probe optical assembly 450 includes an optical path OP that begins from optical fiber end 324 and that generally follows the substantially co-axial axes A1 through A5. In an example, optical fiber end 324 defines an object plane OBP and working distance WD defines the distance where light-deflecting-member axis A5 intersects axis A4 to an image plane IMP where the smallest image spot 652 is formed. The optical path OP thus comprises the path over which light 650 travels from object plane OBP to image plane IMP.

OCT Probe

Figure 9A:
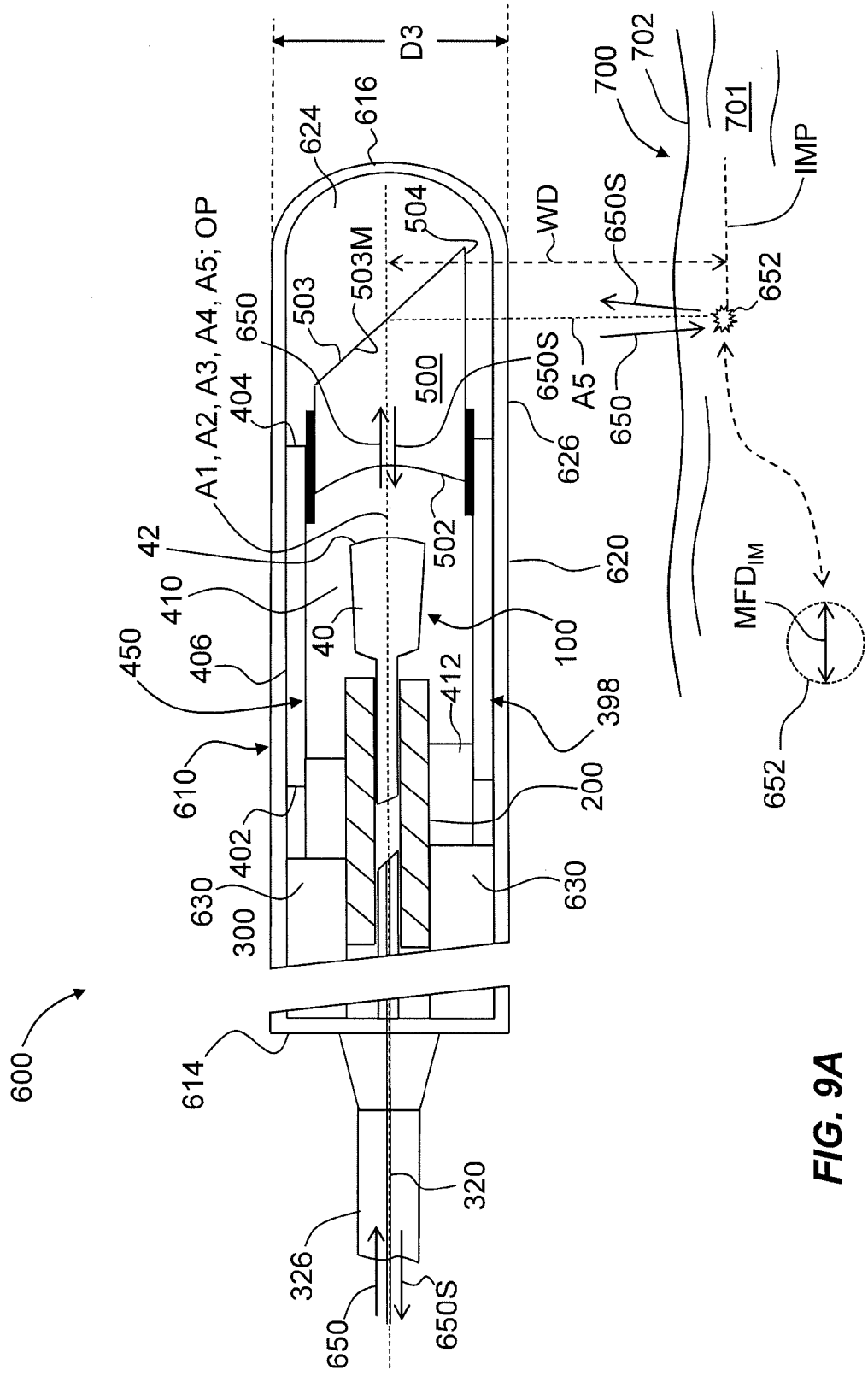
FIG. 9A is a cross-sectional view of an example OCT probe that utilizes the probe optical assembly of FIG. 8B.

FIG. 9A is similar to FIG. 8B and shows an example of an OCT probe ("probe") 600 that includes a long (e.g., several meters long) transparent jacket 610 into which probe optical assembly 450 and optical fiber 320 are inserted. An example jacket 610 has a cylindrical body portion 620 that defines an interior 624. In an example, jacket 610 comprises a long polymer tube having a rounded distal end 616. The cylindrical body portion 620 has a cylindrically curved outer surface 626. In an example, jacket 610 has a diameter D3 in the range 1 mm≤D3≤2 mm.

The jacket 610 is configured to contain probe optical assembly 450 in interior 624. FIG. 9A also shows an example where jacket 610 includes a proximal end 614 at which an optical fiber cable 326 that carries optical fiber 320 is operably connected to the jacket.

Figure 9B:
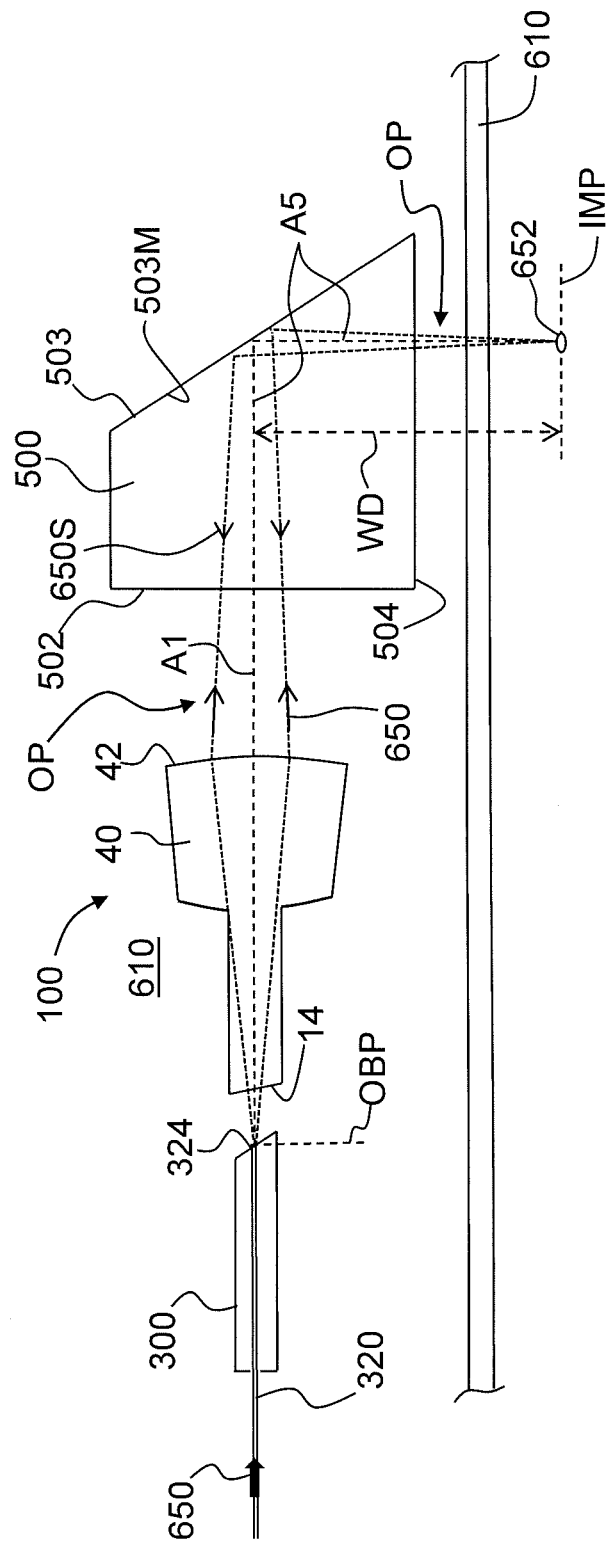
FIG. 9B is a close-up view of the probe optical assembly contained within the interior of the jacket of probe, showing incident light and scattered light traversing the optical path in opposite directions.

FIG. 9B is a close-up view of the probe optical assembly 450 contained within interior 624 of jacket 610 of probe 600 and shows light 650 and scattered light traversing optical path OP in opposite directions. The light 650 originates from light source LS, which is optically coupled to end 323 of optical fiber 320. In an example, light 650 from light source LS has a wavelength of about 1.3 um. The use of a single-mode optical fiber provides the necessary spatial coherence for OCT applications.

With reference to FIG. 9A and FIG. 9B, light 650 from light source LS initially travels down optical fiber 320 as guided light. This guided light 650 exits optical fiber end 324 at or near ferrule end 304 and diverges as it begins traveling over optical path OP. This divergent light then passes through gap 210G and enters proximal end 14 of stub section 110 of stub lens element 100. The divergent light 650 then travels through stub section 110 to lens 40, where it exits the lens at lens surface 42 and passes to light-deflecting member 500. Note that lens surface 42 has positive optical power and so acts to converge light 650. The now convergent light 650 enters light-deflecting member 500 at curved surface 502, and is then totally internally reflected at TIR mirror 503M within the light-deflecting member. This reflection directs convergent light 650 to continue traveling along axis A5 and to exit light-deflecting member 500 at bottom surface 504. The light 650 then passes through cylindrical body portion 620 of transparent jacket 610 that resides adjacent light-deflecting member bottom surface 504 and exits probe 600. Thus, optical path OP passes through transparent jacket 610.

It is noted here that cylindrical curvature of cylindrical body portion 620 of jacket 610 acts as a cylindrical lens surface and so has first optical power in one direction. Accordingly, in an example, cylindrically curved front surface 502 of light-deflecting member 500 is configured to have second optical power that compensates for the first optical power. In an example, this compensation can be provided as negative optical power (i.e., a 1D concave surface) on surface 502 in the same plane of curvature as cylindrical body portion 620 or as positive optical power (i.e., a 1D convex surface) in the plane of curvature orthogonal to the cylindrical body portion. Thus, in one case, the same negative (diverging) optical effect is introduced in both axes, while in another case, the positive (converging) optical effect compensates for the diverging effect of the curved outer surface 626 of jacket 610. Surface 502 of light-deflecting member 500 can be made curved using standard micro-polishing and micro-finishing techniques.

The light 650 that exits probe 600 then travels to a sample 700, which resides adjacent the probe as shown in FIG. 9A. The sample 700 has a body (volume) 701 that defines a sample surface 702. The convergent light 650 is substantially brought to a focus at working distance WD by virtue of lens surface 42 of stub lens element 100 having the aforementioned positive optical power. The focused light 650 forms image spot 652, which has associated image $MFD_{IM}$, as illustrated in the close-up inset view of the image spot.

A portion 650S of light 650 incident upon sample 700 is scattered back from sample surface 702 or volume 701 into probe optical assembly 450 through the cylindrical body portion 620 of transparent jacket 610. This scattered light 650S then travels back through probe optical assembly 450 over optical path OP but in the reverse direction to that of incident light 650. The scattered light 650 is then diverted upstream from optical fiber 320 by a fiber coupler FC to travel in another optical fiber section 318 (FIG. 8B) to be interfered with reference light (not shown). The interfered light is then detected and processed according to conventional OCT procedures.

The stub lens element 100 serves to receive light 650 emitted from optical fiber end 324 and form a high-quality Gaussian beam. In an example, stub lens element 100 and light-deflecting member 500 are configured to meet the requirements for the image mode-field diameter (MFD) and working distance WD for OCT applications. The angled optical fiber end 324 and angled end 14 of stub section 110 serve to reduce back reflections [and thereby?] to improve the SNR. As discussed above, gap 210G between angled ferrule end 324 and ferrule and angled end 14 of stub section 110 can be filled with an index-matching material to further reduce back reflections as well as to reduce the sensitivity of the rotational alignment of the opposing angled ends that define the gap.

Design Considerations

Figure 10:
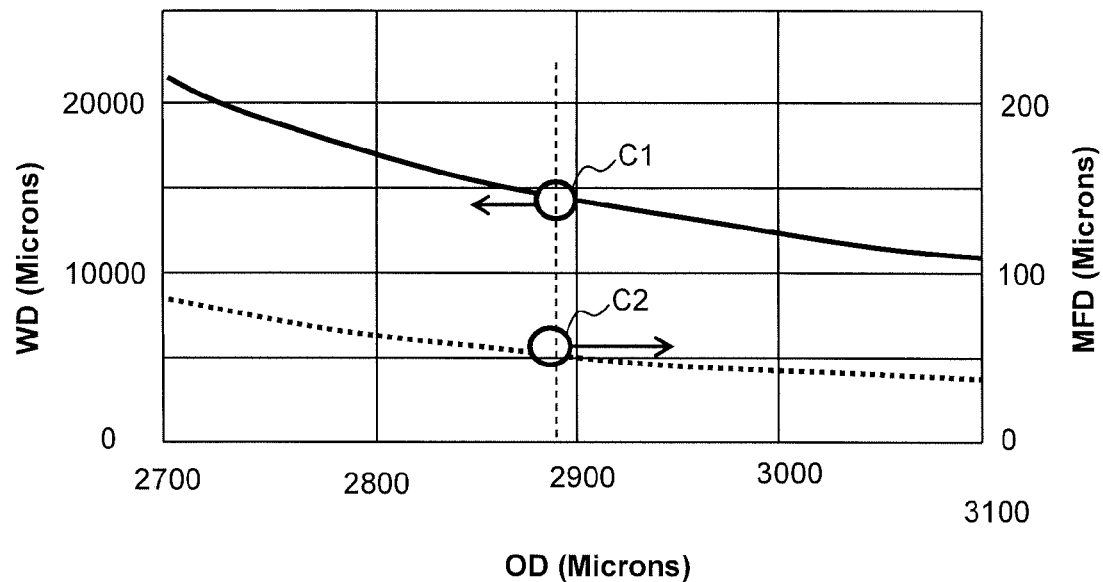
FIG. 10 plots the object distance OD (horizontal axis) vs. the working distance WD (left vertical axis, solid-line curve) and the mode field diameter MFD (right vertical axis, dotted-line curve) in connection with designing an example stub lens element, with all dimensions being in microns.

FIG. 10 plots the object distance OD (horizontal axis) vs. the working distance WD (left vertical axis, solid-line curve) and the mode field diameter MFD (right vertical axis, dotted-line curve) in connection with designing an example stub lens element 100. All dimensions are in microns. A Gaussian beam for light 650 was used, along with a radius of curvature of 0.75 mm for lens surface 42, and silica as the optical material. The wavelength of light 650 was 1.3 microns, at which silica has a refractive index n of about 1.45.

Based on the plot of FIG. 10, in order to have a working distance WD of about 13.5 mm, the object distance OD needs to be about 2890 microns. The corresponding image $MFD_{IM}$ is about 60 microns.

The plot of FIG. 10 can also be used to determine the tolerances needed for this design to control working distance WD to within certain limits. As can be seen by a circle C1 provided on the solid-line curve, object distance OD needs to be controlled to better than about 10 microns in order to control working distance WD to better than 500 microns. Likewise, with reference to a circle C2 on the dotted-line curve, controlling object distance OD to within 10 microns controls mode field diameter MFD to within about 25 microns. Like plots can be made for the tolerances on the radius of curvature of lens surface 42. These kinds of tolerance assessments indicate the need for very tight control of working distance WD if good OCT imaging is to be obtained.

In OCT applications, the transverse imaging resolution depends on image $MFD_{IM}$ of image spot 652 formed at working distance WD. A smaller image spot 652 with the same working distance WD is thus desired to achieve higher imaging resolution.

Figure 11:
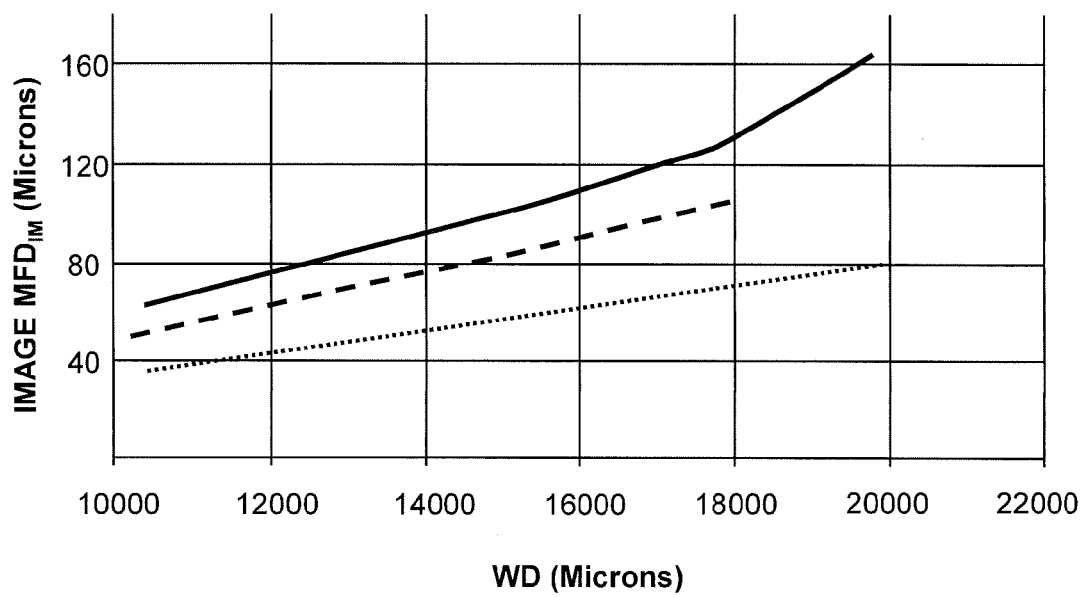
FIG. 11 is a plot similar to that of FIG. 10 that plots the image $MFD_{IM}$ (microns) versus the working distance WD (microns) for the case of a single-mode optical fiber, but where the fiber $MFD_F$ is changed from 10 um to 7 um.

FIG. 11 is similar to FIG. 10 and plots the image $MFD_{IM}$ (microns) versus the working distance WD (microns) for the case of a single-mode optical fiber 320, but where the input fiber $MFD_F$ is changed from 10 microns to 7 microns. The solid line and dashed line curves represent two different glass types for stub lens element 100, namely, PYREX and silica, which has a lower index than PYREX. The dotted line indicates the results with a smaller mode field fiber. The curves plotted in FIG. 11 indicate that the smaller fiber MFDF leads to a smaller image $MFD_{IM}$ at the same working distance WD. Similarly, a smaller refractive index n for stub lens element 100 (for example, silica vs. PYREX) leads to a smaller image $MFD_{IM}$.

Figure 12:
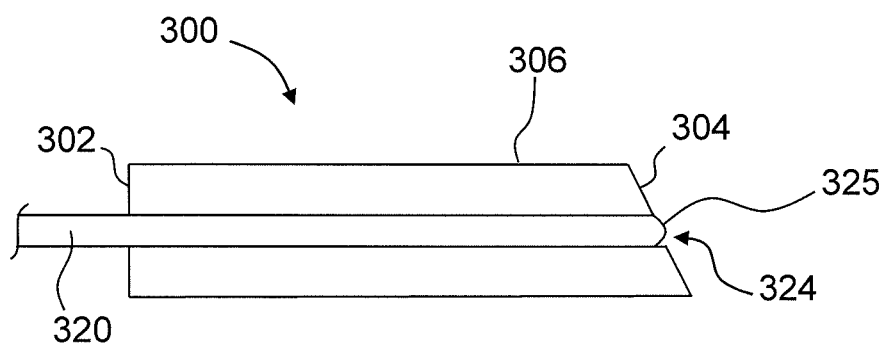
FIG. 12 is similar to FIG. 7B and illustrates an example modification of the optical fiber by providing a lens at the optical fiber end either by re-shaping the otherwise flat optical fiber end or by adding a separate lens element.

FIG. 12 is similar to FIG. 7B and illustrates an example modification of optical fiber 320 at optical fiber end 324. In the example, rather than using an optical fiber 320 having a smaller core diameter, a lens 325 is formed on (e.g., via re-shaping via acid etching or melting) or is otherwise added directly to optical fiber end 324. The lens 325 can have any one of a variety of surface shapes, including spherical and aspherical. Example aspherical surface shapes include parabolic shapes, hyperbolic shapes, biconic shapes, and the like. The shape of lens 325 is limited only by current optical fiber lens-forming techniques.

The lens 325 is configured to reduce fiber $MFD_F$, which in turn reduces image $MFD_{IM}$. Example specifications for image $MFD_{IM}$, working distance WD, and the $M^2$ parameter for light 650 are about 80 microns, about 13.5 mm to 15 mm and less than 1.3, respectively. Embodiments of probe 600 fabricated using the components, assemblies and methods as described herein can readily meet these specifications.

Figure 13A:
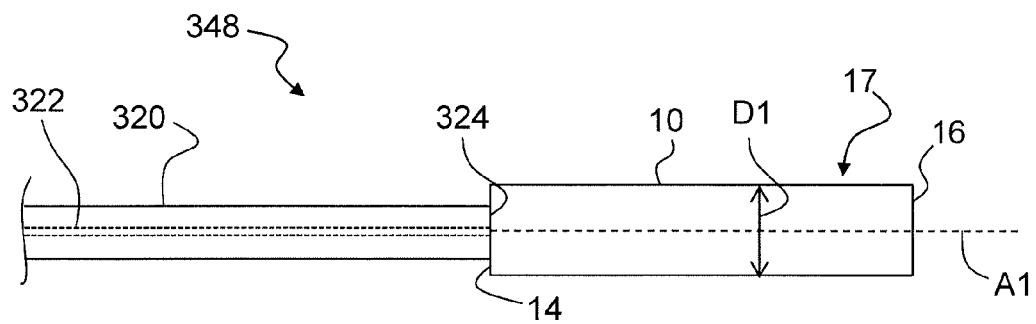
FIG. 13A through FIG. 13C illustrate an example method of forming a fiber pigtail lens assembly using a fusion splicing process.
Figure 13B:
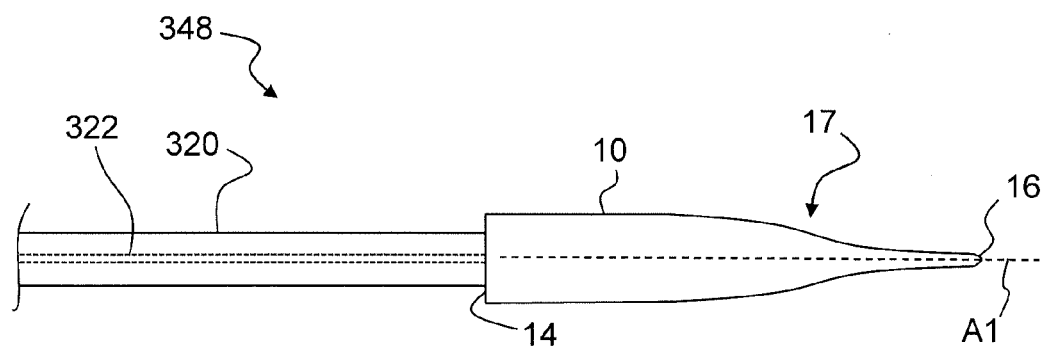
Figure 13C:
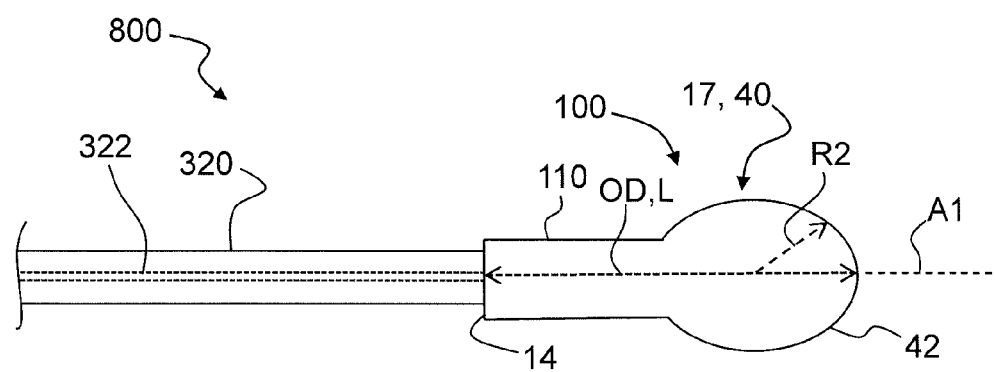

FIG. 13A through FIG. 13C illustrate an example method of forming a fiber pigtail lens assembly 800 that can serve as a more compact version of the previously described stub lens assembly 350. With reference first to FIG. 13A, optical fiber 320 is spliced at optical fiber end 324 to end 14 of rod 10. The optical fiber 320 has a core 322, which in an example is comprised of silica or doped silica. In an example, rod 10 is made of silica so that optical fiber core 322 and the rod are substantially index matched. Splicing optical fiber 320 to rod 10 forms a contiguous fiber pigtail structure 348 that is further processed to form fiber pigtail lens assembly 800. The general process for forming this monolithic fiber pigtail structure 348 is described in U.S. Pat. Nos. 7,228,033 B2, 7,258,495 B1 and 6,904,197 B2, which are incorporated by reference herein.

With reference now to FIG. 13B, rod distal end portion 17 is processed to have a tapered shape and so that rod 10 has a select length to within about +/−20 microns. By controlling the shape of rod distal end portion 17, the subsequent lens 40 can be made to have a select configuration.

With reference now to FIG. 13C, monolithic fiber pigtail structure 348 of FIG. 13B is further processed using for example the thermal methods described above so that rod distal end portion 17 becomes bulbous and forms lens 40 with lens surface 42 having a nominal radius of curvature R2. Thus, the resulting fiber pigtail lens assembly 800 includes a stub lens element 100 that includes stub section 110 spliced at end 14 to optical fiber 320. In fiber pigtail lens assembly 800, the object distance OD is now essentially the axial distance or length L of the newly formed stub lens element 100, wherein L is the distance from proximal end 14 of stub section 110 to the apex of lens surface 42 of lens 40. In an example, length L is in the range 0.5 mm to 5.0 mm.

Figure 13D:
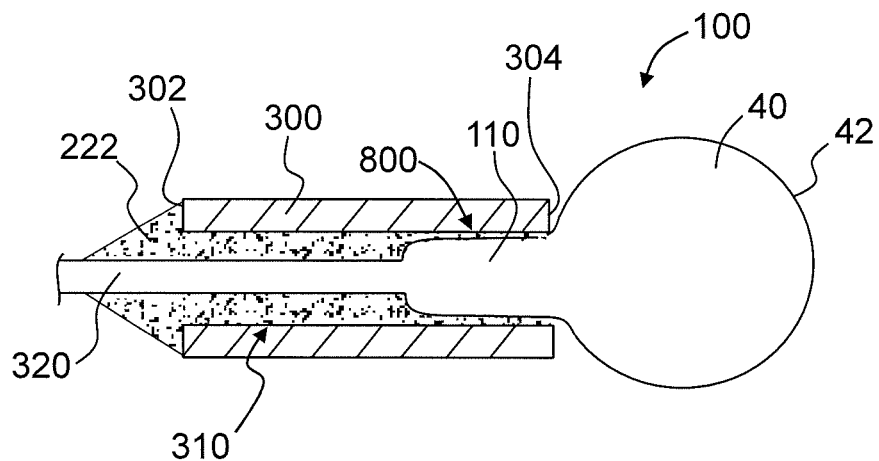
FIG. 13D is similar to FIG. 13C and shows the fiber pigtail assembly operably engaged with the ferrule so that the lens is adjacent one of the ferrule ends.

FIG. 13D is similar to FIG. 13C and shows the fiber pigtail assembly 800 operably engaged with ferrule 300 so that lens 40 is adjacent ferrule end 304. Adhesive material 222 is included within central bore 310 and is used to fix stub section 110 and the spliced-end portion of optical fiber 320 within the ferrule channel.

Figure 13E:
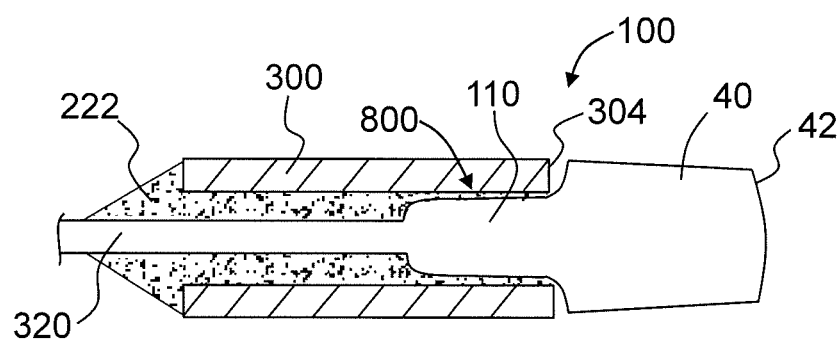
FIG. 13E is similar to FIG. 13D and shows an example embodiment where the lateral dimension of the lens has been reduced in size.

FIG. 13E is similar to FIG. 13D and shows an example embodiment where lens 40 has been reduced in size by polishing, turning, grinding or like manner. This makes fiber pigtail assembly 800 smaller in the lateral dimension, which allows it to be used in different configurations where a wider bulbous lens 40 might prove problematic. For example, with reference to FIG. 13F, the fiber pigtail assembly 800 and ferrule 300 are shown operably supported by support member 398 in the form of a transparent support substrate 820 having an upper surface 828. In an example, support substrate 820 supports an example light-deflecting member 500 in the form of a prism atop upper surface 828 adjacent one end of the substrate. The support substrate 820 also supports fiber pigtail assembly 800 and ferrule 300 on surface 828 near the other end of the support substrate. In an example, support substrate 820 has a thickness of about 190 microns.

In the example shown, light-deflecting member 500 now has a planar light-deflecting member front surface 502, along with the aforementioned angled surface 503 that defines a TIR mirror 503M, and bottom surface 504, which now resides adjacent the substrate upper surface 828. The fiber pigtail assembly 800 is disposed on upper surface 828 and in an example is secured thereto, e.g., with adhesive material 222. The fiber pigtail assembly 800 is arranged so that lens surface 42 of lens 40 confronts planar light-deflecting-member surface 502. The light-deflecting member TIR mirror 503M serves to fold axis A1 so that optical path OP passes through support substrate 820 at the location adjacent light-deflecting member bottom surface 504.

In an example, light-deflecting member 500 can be formed by providing a blank (also called a preform) having a triangular cross-section and that can include a corresponding surface that has either a convex or concave curvature, depending on how the compensation for curved jacket 610 is to be carried out via the subsequently formed light-deflecting member. The blank is then drawn into rods using standard glass drawing techniques, wherein the rods have the same cross-sectional shape as the blank.

Figure 13F:
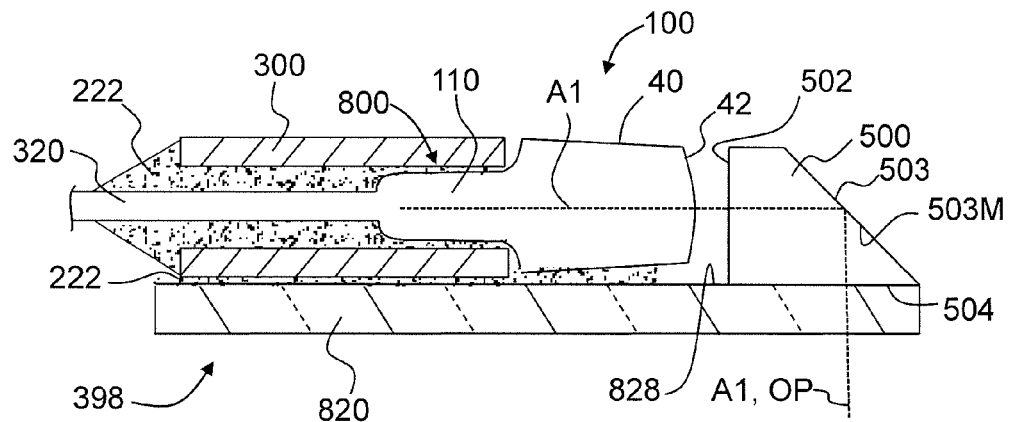
FIG. 13F shows the fiber pigtail assembly of FIG. 13E as arranged in a ferrule, with the ferrule and fiber pigtail operably disposed on a transparent support substrate adjacent a light-deflecting member.

This light-deflecting member fabrication method requires shaping one blank from which hundreds of meters of light-deflecting-member rods can then be drawn. Centimeter lengths of the light-deflecting-member rods can be mounted on support substrate 820 and then diced into individual light-deflecting members and substrates such as shown in FIG. 13F In an example, the blank is formed so that light-deflecting-member surface 502 has the appropriate curvature. Moreover, in an example, light-deflecting-member surface 502 can have an amount of tilt relative to light-deflecting member axis A5 that is capable of reducing back reflections. For example, for most anticipated OCT applications, a tilt of about 2 degrees is sufficient for reducing back reflections to as low as −50 dB to −60 dB.

Figure 14:
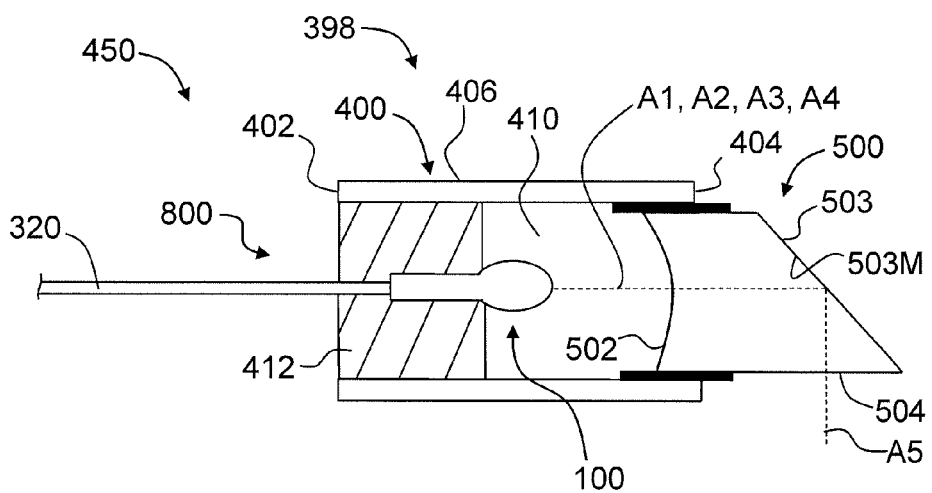
FIG. 14 is similar to FIG. 8B and illustrates an example embodiment of the probe optical assembly that employs a fiber pigtail lens assembly in place of the stub lens assembly.

FIG. 14 is similar to FIG. 8B and illustrates an example embodiment of probe optical assembly 450 that employs fiber pigtail lens assembly 800 in place of the aforementioned stub lens assembly 350. The fiber pigtail lens assembly 800 is shown being held in place within outer sleeve 400 by retaining feature 412. The use of fiber pigtail lens assembly 800 simplifies the design and assembly of probe optical assembly 450 and also eliminates gap 210G, which was present in stub lens assembly 350 described above. The configuration of fusion-spliced fiber pigtail lens assembly 800 reduces the amount of back reflection to an acceptable level without the need for angled facets. This contributes to pigtail lens assembly 800 having robust performance while also having a relatively low assembly cost. FIG. 14 also shows an example of light-deflecting member 500 operably engaged at end 404 of outer sleeve 400. In an example, light-deflecting member 500 can be molded or embossed to sleeve 400 using polymers or UV curable epoxies.

The fiber pigtail lens assembly 800 is relatively tolerant to process variations. The underlying reason for this has to do with the fact that the amount of optical material needed to form lens 40 is proportional to the cube of the lens radius R2, whereas the amount of material contained in the cylindrical stub section 110 is proportional to the square of the rod radius R1, wherein R1=(D1)/2. For OCT imaging, an example lens radius R2 for lens 40 of fiber pigtail lens assembly 800 is in the range about 750 microns to about 800 microns. In an example, rod 10 from which lens 40 is formed has a diameter D1 in the range of about 350 microns to about 500 microns.

Figure 15:
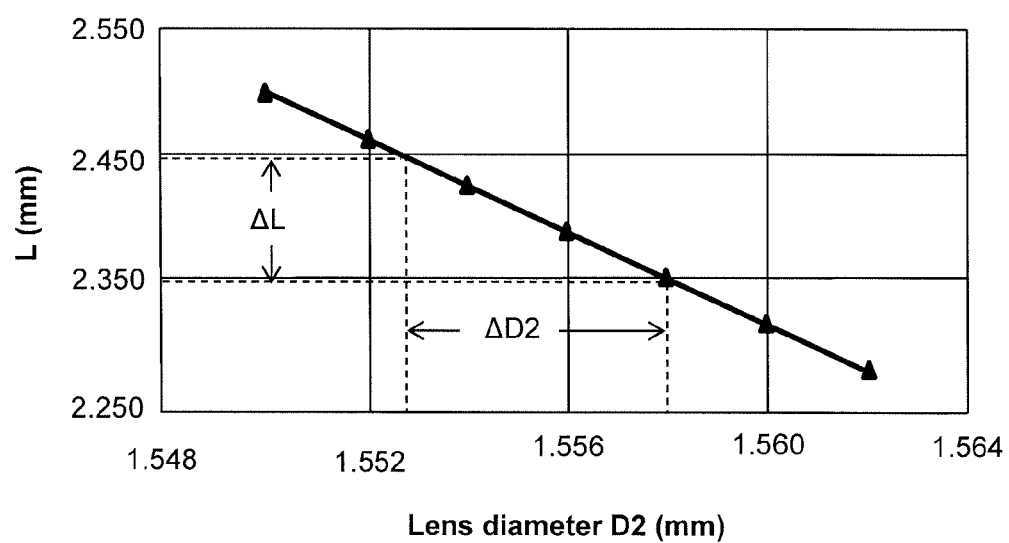
FIG. 15 is a plots the relationship between the length L (mm) of a stub lens element and the lens diameter D2 (mm) of the stub lens element.

A variation in the length L of stub lens element 100 is dictated by the shortening of rod 10 during the formation of lens 40. FIG. 15 plots the relationship between the stub lens element length L (mm) and the diameter D2 (mm) of lens 40 of stub lens element 100. The total variation in length L is ostensibly determined by the accuracy of the mechanism used to feed rod 10 into heat source 20 during the lens formation process (see FIG. 1). Even with a change in length ΔL of 50 microns, the corresponding change in the lens diameter ΔD2 is only about 2.5 microns. This amount of change in the diameter D2 of lens 40 does not lead to a significant change in the focusing characteristics of the lens, so the working distance WD and image $MFD_{IM}$ remain substantially unchanged.

Figure 16A:
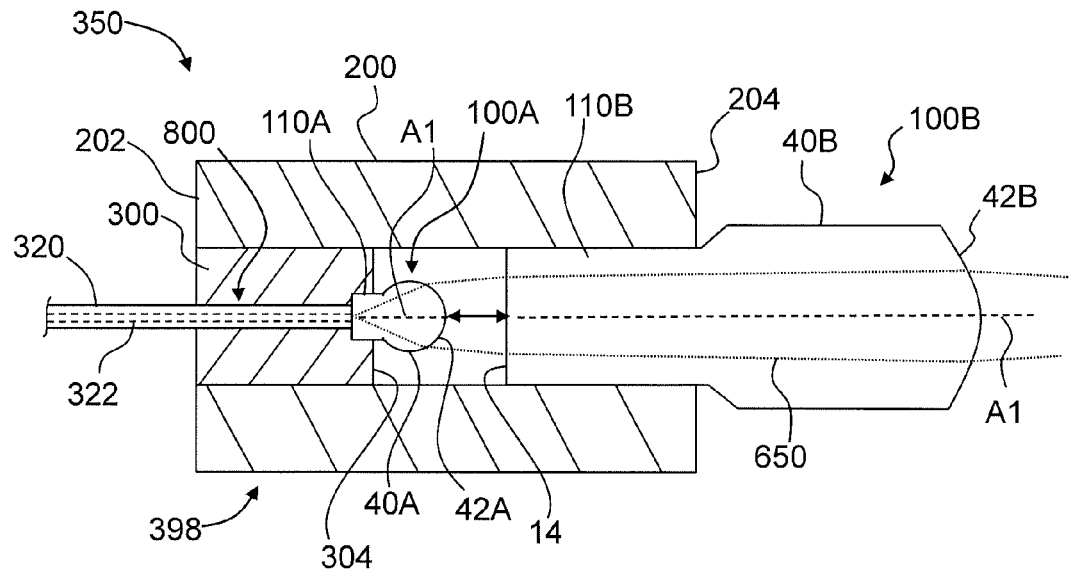
FIG. 16A is a cross-sectional view of another example embodiment of the stub lens assembly that includes the fiber pigtail lens assembly that has a first fused fiber lens element in combination with a second stub lens element.

FIG. 16A is a cross-sectional view of another example embodiment of stub lens assembly 350 that includes fiber pigtail lens assembly 800, wherein its fused stub lens element is denoted as 100A (with lens 40A, lens surface 42A, etc.), as used in combination with a second stub lens element, which is denoted as 100B (with lens 40B, lens surface 42B, etc.). The support member 398 in the form of inner sleeve 200 operably supports ferrule 300 at first end 202 and operably supports stub lens element 100B at second end 204.

This configuration of stub lens assembly 350 now has two optical surfaces with optical power, namely stub lens surfaces 42A and 42B. The stub lens surfaces 42A and 42B are arranged in stub lens assembly 350 so that they are confronting. The fiber $MFD_F$ associated with fiber pigtail lens assembly 800 in this example can be made relatively small. This in turn allows for optical fiber 320 to be a conventional optical fiber, such as SMF-28® optical fiber, which is available from Corning, Inc., Corning, N.Y., and which has a core diameter of nominally 10 microns.

Another advantage is that the amount of back scattering of light 650 is relatively low by virtue of the pigtail configuration of fiber pigtail lens assembly 800. Also, the two lenses 40A and 40B can be configured so that light 650 is substantially collimated as it travels from lens surface 42A to lens surface 42B, as illustrated in FIG. 16A. This can serve to reduce any beam distortions and also to reduce the diameter requirements for lens 40B of stub lens element 100B.

Figure 16B:
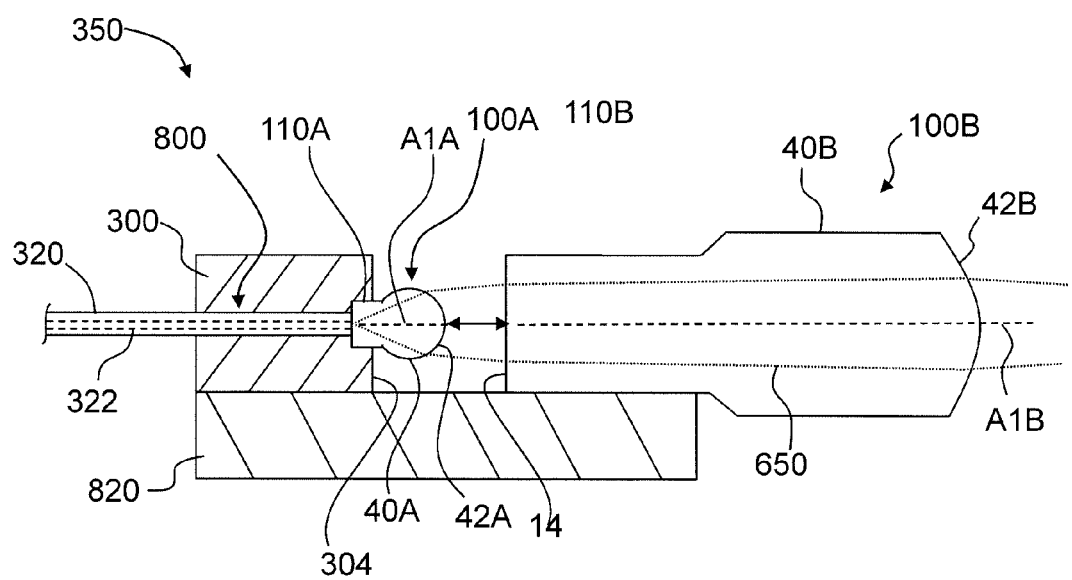
FIG. 16B is similar to FIG. 16A, but with the outer sleeve replaced by a support substrate.

FIG. 16B is similar to FIG. 16A and illustrates an example embodiment of stub lens assembly 350 wherein outer sleeve 200 is replaced with support substrate 820. The support substrate 820 can be made of a rigid material such as glass, plastic, metal and the like.

Figure 17:
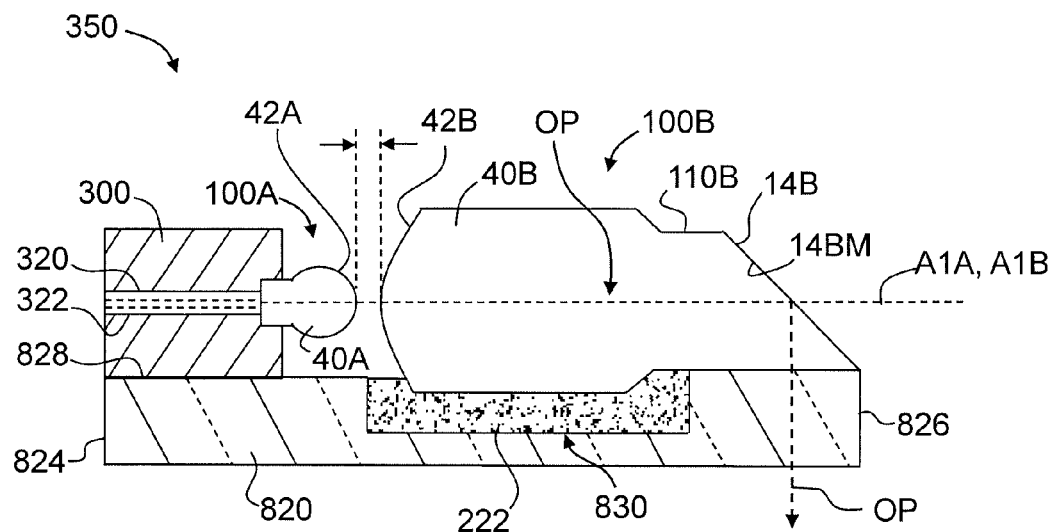
FIG. 17 is similar to FIG. 16B and illustrates another example embodiment of a fused lens assembly wherein the support substrate is made of a transparent material, and the second stub lens has an angled surface that serves as a total-internal-reflection (TIR) mirror.

FIG. 17 is similar to FIG. 16B and illustrates another example embodiment of stub lens assembly 350 wherein support substrate 820 is made of a transparent material. In an example, support substrate 820 is formed as a unitary molded piece that includes first and second ends 824 and 826, and a recess 830 formed in upper surface 828. The ferrule 300 with fiber pigtail lens assembly 800 engaged therewith is disposed on upper surface 828 of support substrate 820 adjacent end 824. Likewise, stub lens element 100B is disposed on upper surface 828 of support substrate 820 adjacent end 826, with the stub lens surface 42B in opposition to stub lens surface 42A. Stub lens element 100B has an angled distal end 14B that defines a TIR mirror 14BM.

The stub lens elements 100A and 100B are aligned (i.e., their respective axes A1A and A1B are made co-linear) using for example the aforementioned method of monitoring of the image $MFD_{IM}$ (see FIG. 7C). Once so aligned, they are fixed in position. In an example, stub lens element 100B can be secured to support substrate 820 by an adhesive material 222 introduced into recess 830, where a portion of lens 40B resides. Note that the portion of stub section 110B that includes TIR mirror 14BM serves essentially the same function as the aforementioned separate light-deflecting member 500. The fiber pigtail lens assembly 800 can be axially adjusted within ferrule 300 prior to being fixed in place.

Figure 18:
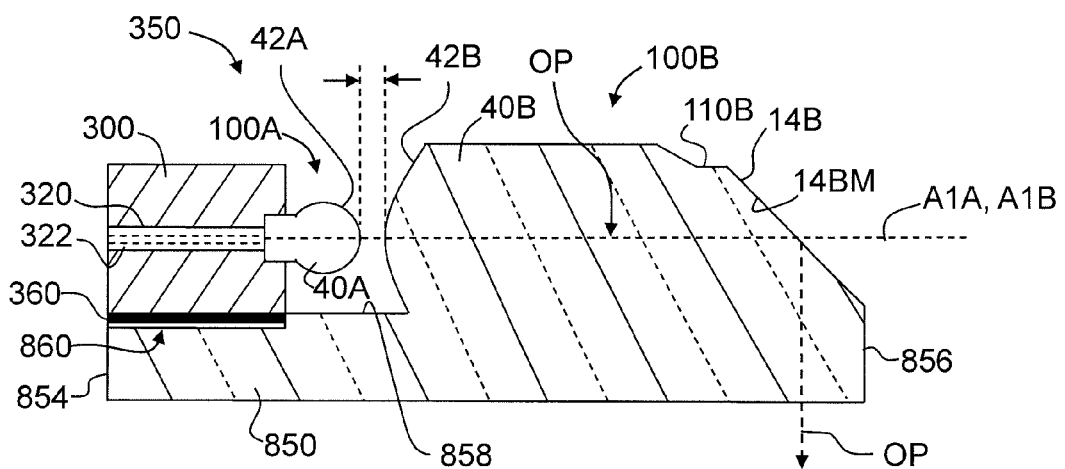
FIG. 18 is similar to FIG. 17 and illustrates an embodiment that includes a transparent monolithic structure that includes a stub lens element portion.

FIG. 18 is similar to FIG. 17 and illustrates an embodiment wherein the support member 398 comprises a transparent monolithic structure 850 that includes ends 854 and 856, and a planar upper surface portion 858 adjacent end 854. The monolithic structure 850 also includes stub lens element portion 100B adjacent end 856, with the stub lens element portion including angled end 14B and TIR mirror 14BM. In an example, planar upper surface portion 858 includes at least one alignment feature 860 that facilitates alignment of ferrule 300 and fiber pigtail lens assembly 800 supported thereby with the stub lens element portion 100B. An example alignment feature 860 is a groove (e.g., a V-groove) that accommodates a corresponding (e.g., complimentary) alignment feature 360 of ferrule 300.

The monolithic structure 850 can be formed, for example, by molding a polymer material, thereby providing for low-cost mass production that can employ reusable molds. The configurations of stub lens assembly 350 of FIG. 18 has the advantage that the beam dimension of light 650 is substantially larger compared to the single mode fiber mode-field diameter before it is incident on lens surface 42B. This substantially reduces the light intensity on the lens surfaces so that they can tolerate much higher power levels without degradation, especially when monolithic structure 850 comprises a polymer material.

Figure 19:
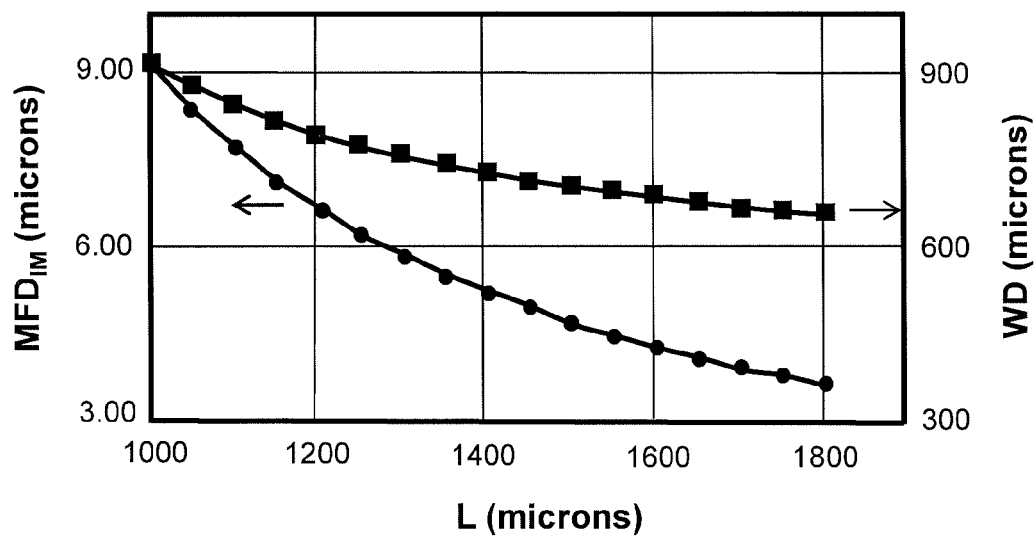
FIG. 19 is a plot of the length L (microns) (horizontal axis) versus the image $MFD_{IM}$ (microns) (left-hand vertical axis) and working distance WD (microns) (right-hand vertical axis) as defined as the beam-waist location, for an example fused lens element suitable for use in the fiber pigtail lens assembly.

FIG. 19 is a plot of the length L (microns) (horizontal axis) versus the image $MFD_{IM}$ (microns) (left-hand vertical axis) and working distance WD (microns) (right-hand vertical axis) as defined as the beam-waist location, for an example stub lens element 100 suitable for use in fused fiber pigtail lens assembly 800. The curve with the circles corresponds to image $MFD_{IM}$ and the curve with the squares corresponds to working distance WD. The plot of FIG. 19 is based on lens 40 having a radius R2=150 microns and optical fiber 320 having a fiber $MFD_F$ of about 10 microns. The plot shows that fiber pigtail lens assembly 800 can have an image $MFD_{IM}$ of about 6.5 microns for a length L of 1,200 microns (1.2 mm).

Figure 20:
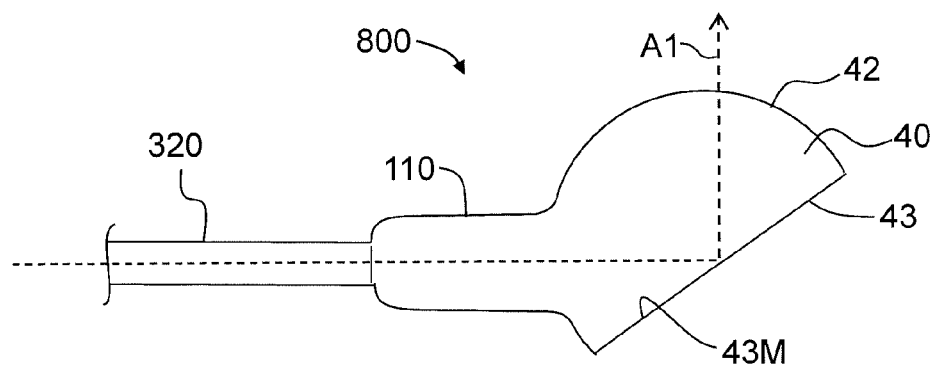
FIG. 20 is a side view of an example fused fiber pigtail lens assembly wherein the lens includes an angled surface that defines a TIR mirror that serves to fold the lens axis and direct it through a portion of the lens surface.

FIG. 20 is a side view of an example fiber pigtail lens assembly 800 wherein lens 40 includes an angled surface (facet) 43 that defines a TIR mirror 43M that serves to fold axis A1 and direct it through a portion of lens surface 42. The facet 43 can also include a curvature to compensate for the defocusing effect of curved outer surface 626 of jacket 610.

Figure 21:
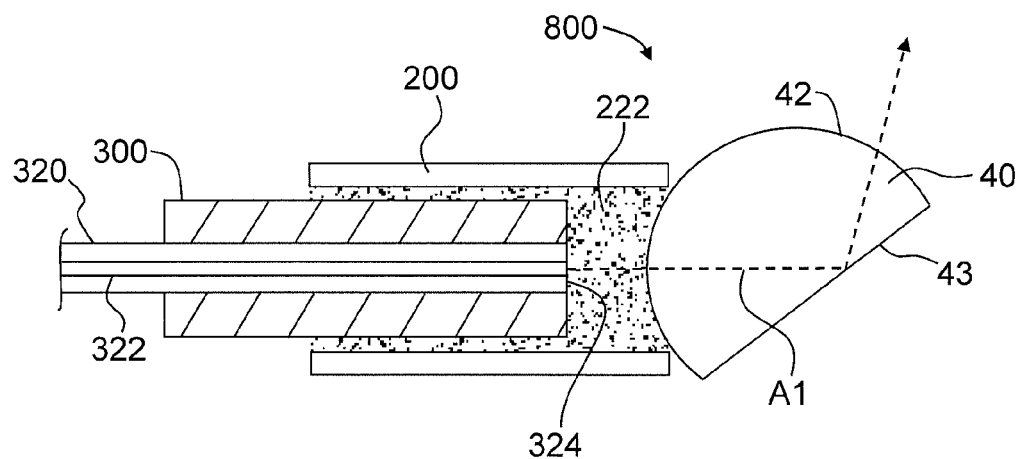
FIG. 21 is similar to FIG. 20 and illustrates another embodiment of the fiber pigtail assembly.

FIG. 21 is another embodiment of the fiber pigtail assembly 800 assembly similar to that shown in FIG. 20, but where optical fiber 320 is not fusion spliced to lens 40. Rather, optical fiber end 324 is spaced apart from lens 40 and is in optical communication therewith through index-matching material 222, e.g., UV epoxy. The optical fiber 320 is shown being supported in ferrule 300, which in turn is supported in inner sleeve 200. As with lens 40 of FIG. 20, lens 40 of FIG. 21 performs both the beam bending at lens surface 42 and the internal reflection at angled surface (facet) 43. In the example of FIG. 21, lens 40 is formed as a single element fabricated from a hemispherical or biconic ball lens made of a glass or a polymer material. With polymer materials, the fabrication of biconic lens or shaped stub lens is generally easier and can be more readily mass produced, e.g., via a molding process.

Although the embodiments herein have been described with reference to particular aspects and features, it is to be understood that these embodiments are merely illustrative of desired principles and applications. It is therefore to be understood that numerous modifications may be made to the illustrative embodiments and that other arrangements may be devised without departing from the spirit and scope of the appended claims.

What is claimed is:

1. A method of making a monolithic stub lens element having a stub section and a lens section, said method comprising:
   heating an end of a rod of optical material that has a central axis and a width dimension D1 in a range between 250 microns and 1000 microns to form a bulbous rod end having a width dimension D2 in a range between 300 microns and 2500 microns wherein the remaining rod defines a stub section;
   removing a portion of the optical material from the bulbous rod end to reduce the width dimension D2 to form a lens having an on-axis lens surface thereby forming a monolithic stub lens element; and
   cutting the stub section to define an angled proximal end opposite the on-axis lens surface.

2. The method of claim 1, wherein the optical material of the rod is one of silica, PYREX, VYCOR, optical glass, or plastic.

3. The method of claim 1, wherein the rod has a circular cross-sectional shape.

4. The method of claim 1, further comprising forming the stub lens element to have an axial length L from the angled proximate end to the lens surface that is in the range 0.5 mm≤L≤5 mm.

5. The method of claim 1, further comprising forming the lens surface to be spherical and having a radius of curvature R2 in the range 0.15 mm≤R2≤1.5 mm.

6. The method of making an optical probe assembly, comprising making the monolithic stub lens element according to claim 1, and further comprising engaging the stub lens element with a first sleeve having first and second ends, an outer surface, a central axis and a central channel that runs along the central axis and that is open at the first and second ends, with the stub section fixed within the central channel.

7. The method of claim 6, wherein the first sleeve comprises a first section of capillary tubing.

8. The method of claim 6, wherein the first sleeve has a slot in the outer surface that leads to the central channel, and further comprising fixing the stub section within the central channel of the first sleeve by introducing an adhesive material into the slot.

9. The method of claim 8, further comprising inserting an optical fiber ferrule that operably supports an optical fiber into the first end of the first sleeve so that an end of the optical fiber resides adjacent the angled proximal end of the stub section within the central channel.

10. The method of claim 9, wherein the optical fiber end resides substantially at the optical fiber ferrule end, and wherein the optical fiber end and optical fiber ferrule end are each angled with an angle different from the angled proximal end of the stub section.

11. The method of claim 9, further comprising:
   focusing light emitted by the optical fiber end at a working distance from the lens surface;
   forming an image spot having an image mode field diameter $MFD_{IM}$; and
   adjusting at least one of the optical fiber end and the stub lens element to minimize the size of the image mode field diameter $MFD_{IM}$.

12. The method of claim 11, further comprising:
  detecting the image spot with a photodetector to form an electrical signal; and
  processing the electrical signal to determine when the image mode field diameter $MFD_{IM}$ is at a minimum.

13. The method of claim 9, further comprising forming a lens on the end of the optical fiber.

14. The method of claim 9, further comprising:
  supporting the optical fiber ferrule, the first sleeve and the stub lens element at a first end of a second sleeve that includes a second end, a central axis and interior open at the first and second ends; and
  disposing a light-deflecting reflective member at the second end of the second sleeve and adjacent the lens surface of the stub lens element so as to be in a cooperative optical relationship therewith, thereby forming a probe optical assembly.

15. The method of claim 14, further comprising forming the light-deflecting member by drawing a blank having substantially the same cross-sectional shape as the light-deflecting member to form a light-deflecting-member rod, and then dicing the light-deflecting-member rod.

16. The method of claim 14, wherein the second sleeve comprises a section of capillary tubing.

17. The method of claim 14, further comprising enclosing the probe optical assembly in a transparent jacket having a diameter D3 in the range 1 mm≤D3≤2 mm.

18. The method of claim 17, wherein the transparent jacket has a curved outer surface that has a first optical power, and further comprising configuring the light-deflecting member to have a second optical power that compensates for the first optical power.

19. The method of claim 17, wherein the transparent jacket comprises a section of polymer tubing.

20. The method of claim 14, wherein the light-deflecting member comprises a prism.

* * * * *